(12) United States Patent
Koh

(10) Patent No.: US 10,281,599 B2
(45) Date of Patent: May 7, 2019

(54) X-RAY APPARATUS AND METHOD OF OPERATING THE SAME

(71) Applicant: Samsung Electronics Co., Ltd, Suwon-si, Gyeonggi-do (KR)

(72) Inventor: Byoung-hoon Koh, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/936,233

(22) Filed: Mar. 26, 2018

(65) Prior Publication Data

US 2018/0217279 A1 Aug. 2, 2018

Related U.S. Application Data

(63) Continuation of application No. 15/462,650, filed on Mar. 17, 2017, now Pat. No. 9,952,339.

(30) Foreign Application Priority Data

Jul. 21, 2016 (KR) .......................... 10-2016-0092897

(51) Int. Cl.
| | |
|---|---|
| H01L 27/146 | (2006.01) |
| G01T 7/00 | (2006.01) |
| G01T 1/17 | (2006.01) |
| A61B 6/00 | (2006.01) |

(52) U.S. Cl.
CPC .............. *G01T 7/00* (2013.01); *A61B 6/4266* (2013.01); *A61B 6/4494* (2013.01); *A61B 6/547* (2013.01); *G01T 1/17* (2013.01); *A61B 6/4283* (2013.01); *A61B 6/4405* (2013.01); *A61B 6/4411* (2013.01); *A61B 6/465* (2013.01); *A61B 6/467* (2013.01)

(58) Field of Classification Search
CPC ..................................... G01T 7/00; G01T 1/17
See application file for complete search history.

(56) References Cited

U.S. PATENT DOCUMENTS

2016/0331334 A1* 11/2016 Imamura .................. A61B 6/06

* cited by examiner

*Primary Examiner* — Kiho Kim

(57) ABSTRACT

Provided are an X-ray apparatus and a method of operating the same. An embodiment provides an X-ray apparatus that displays position information regarding a plurality of X-ray detectors and a method of operating the same. The X-ray apparatus includes a plurality of X-ray detectors, a plurality of mounts to which the plurality of X-ray detectors are mounted, and a work station. The plurality of X-ray detectors include light emitting elements that emit light of colors different from one another, the plurality of mounts include a plurality of light detectors that sense colors of light emitted by the light emitting elements and are disposed apart from one another, respectively. The workstation includes a controller that obtains positional information regarding the plurality of X-ray detectors based on colors of light sensed by the light detectors respectively included in the plurality of mounts.

19 Claims, 19 Drawing Sheets

X-RAY APPARATUS AND METHOD OF OPERATING THE SAME

CROSS-REFERENCE TO RELATED APPLICATIONS AND CLAIM OF PRIORITY

The present application is a continuation of U.S. application Ser. No. 15/462,650, filed Mar. 17, 2017, which claims foreign priority to Korean Patent Application No. 10-2016-0092897, filed on Jul. 21, 2016, the disclosures of which are incorporated by reference in their entireties.

TECHNICAL FIELD

The present disclosure relates to an X-ray apparatus and a method of operating the same, and more particularly, to an X-ray apparatus for providing a user with information regarding a position of an X-ray detector used for X-ray scanning and a direction in which the X-ray detector is mounted to a frame of the X-ray apparatus, and a method of operating the same.

BACKGROUND

An X-ray is an electromagnetic wave having a wavelength from about 0.01 to about 100 angstrom (Å) and can be used to obtain the internal structure of an object. Therefore, X-ray devices are widely used for photographing the inside of a living body or for common non-destructive industrial inspection.

The basic principle of a photographing device using X-rays is to transmit X-rays emitted by an X-ray tube (or an X-ray source) to a target object and detect a difference in the intensity of the transmitted X-rays via an X-ray detector and thus obtain the internal structure of the target object. When an X-ray apparatus includes a plurality of X-ray detectors, it is necessary for a user to check which of the X-ray detectors is mounted to a frame of the X-ray apparatus or a direction the corresponding X-ray detector is mounted to the frame of the X-ray apparatus.

SUMMARY

To address the above-discussed deficiencies, it is a primary object to provide an X-ray apparatus including a plurality of X-ray detectors, the X-ray apparatus having high user's convenience by providing positional information regarding the plurality of X-ray detectors to a user taking an X-ray image of a target object by using the plurality of X-ray detectors.

Additional aspects will be set forth in part in the description which follows and, in part, will be apparent from the description, or may be learned by practice of the presented embodiments.

According to an aspect of an embodiment, an X-ray apparatus includes a plurality of X-ray detectors, a plurality of mounts to which the plurality of X-ray detectors are mounted, and a work station. The plurality of X-ray detectors include light emitting elements that emit light of colors different from one another, the plurality of mounts include a plurality of light detectors that sense colors of light emitted by the light emitting elements and are disposed apart from one another, respectively. The workstation includes a controller that obtains positional information regarding the plurality of X-ray detectors based on colors of light sensed by the light detectors respectively included in the plurality of mounts.

For example, the light emitting elements may include light emitting diodes (LED) and are arranged on first sides of the plurality of X-ray detectors, respectively.

For example, the plurality of mounts may include a stand-type mount or a table-type mount, and the controller may obtain information regarding at least one of a position of a first X-ray detector mounted to the stand-type mount, a position of a second X-ray detector mounted to the table-type mount, and a position of a third X-ray detector mounted to neither the stand-type mount nor the table-type mount.

For example, the workstation may further include a display for displaying positional information regarding the plurality of X-ray detectors in a user interface (UI) including at least one of letters, numbers, symbols, colors, and images.

For example, the workstation may further include a user input unit for receiving a user input for selecting a scan mode for performing X-ray scanning using any one of a stand-type mount, a table-type mount, and a portable type X-ray detector, and the controller may recognize position of the X-ray detector, which indicates whether an X-ray detector is mounted to a mount according to the scan mode selected based on the user input, and determine whether it is possible to perform X-ray photographing according to the scan mode selected based on the user input, based on the recognized position of the X-ray detector.

For example, the display may display information indicating the determined X-ray scan possibility via the user interface.

For example, each of the plurality of X-ray detectors may further include a communicator for transmitting identification information regarding each of the plurality of X-ray detectors to the workstation, and the identification information may include at least one of unique information including at least one of MAC addresses and serial numbers of the plurality of X-ray detectors and specification information including at least one of sizes of the plurality of X-ray detectors and types of mounts for mounting the plurality of X-ray detectors.

For example, the workstation may further include a communicator for receiving identification information from each of the plurality of X-ray detectors, and the controller may assign different colors of light to the plurality of X-ray detectors according to the identification information, respectively.

For example, the communicator may transmit information regarding the assigned colors of light to the plurality of X-ray detectors, respectively, and the light emitting elements included in the plurality of X-ray detectors may respectively emit light of colors according to the information regarding the assigned colors of light transmitted from the workstation.

For example, the plurality of light detectors may sense intensity of light emitted by the light emitting elements and, based on intensity of light sensed by a first light detector disposed at a location to face a first side of a first X-ray detector mounted to a first mount from among the plurality of light detectors included in the first mount, the controller may obtain information regarding a direction in which the first X-ray detector is mounted to the first mount.

For example, the controller may obtain mounting direction information indicating whether the first X-ray detector is mounted to the first mount in the landscape-direction or the portrait-direction.

Each of the plurality of X-ray detectors may further include a reflective member that is disposed adjacent to the light emitting element, the plurality of mounts may further include a plurality of light sources that are respectively disposed adjacent to the plurality of light detectors and emit light, and the controller may obtain information regarding intensity of light that is emitted by a plurality of light sources included in the first mount from among the plurality of light sources and reflected by the reflective member disposed on the first side of the first X-ray detector mounted to the first mount from a light sensor of the first mount and recognize a direction in which the first X-ray detector is mounted to the first mount based on the information regarding the intensity of the light.

According to an aspect of another embodiment, a method of operating an X-ray apparatus is provided that includes a plurality of X-ray detectors, a plurality of mounts to which the plurality of X-ray detectors are mounted, and a work station. The method includes receiving information regarding colors of light emitted by a plurality of light emitting elements respectively included in the plurality of X-ray detectors from a plurality of light detectors respectively included in the plurality of mounts. The method also includes obtaining positional information regarding the plurality of X-ray detectors based on the received information regarding the colors of light. The method also includes displaying the positional information regarding the plurality of X-ray detectors in a user interface (UI) including at least one of letters, numbers, symbols, colors, and images.

For example, the plurality of mounts may include a stand-type mount or a table-type mount and, in the obtaining of the positional information regarding the plurality of X-ray detectors, information regarding at least one of a position of a first X-ray detector mounted to the stand-type mount, a position of a second X-ray detector mounted to the table-type mount, and a position of a third X-ray detector mounted to neither the stand-type mount nor the table-type mount may be obtained.

For example, the method may further include receiving a user input for selecting a scan mode for performing X-ray scanning using any one of a stand-type mount, a table-type mount, and a portable type X-ray detector; recognizing position of the X-ray detector, which indicates whether an X-ray detector is mounted to a mount according to the scan mode selected based on the user input; and determining whether it is possible to perform X-ray scanning according to the scan mode selected based on the user input, based on the recognized position of the X-ray detector.

For example, the method may further include displaying information indicating the determined X-ray scan possibility via the user interface.

For example, the method may further include receiving identification information regarding each of the plurality of X-ray detectors from the plurality of X-ray detectors, wherein the identification information may include at least one of unique information including at least one of MAC addresses and serial numbers of the plurality of X-ray detectors and specification information including at least one of sizes of the plurality of X-ray detectors and types of mounts for mounting the plurality of X-ray detectors.

For example, the method may further include assigning different colors of light to the plurality of X-ray detectors according to the identification information, respectively; and transmitting information regarding the assigned colors of light to the plurality of X-ray detectors, respectively.

For example, the method may further include sensing intensity of light emitted by the light emitting elements; and, based on the sensed intensity of light, obtaining information regarding directions in which the plurality of X-ray detectors are mounted to the plurality of mounts.

For example, in the obtaining of the information regarding the directions in which the plurality of X-ray detectors are mounted to the plurality of mounts, mounting direction information indicating whether the first X-ray detector is mounted to the first mount in the landscape-direction or the portrait-direction may be obtained.

According to an aspect of another embodiment, there is provided a non-transitory computer readable recording medium having recorded thereon a computer program for implementing the above described method.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
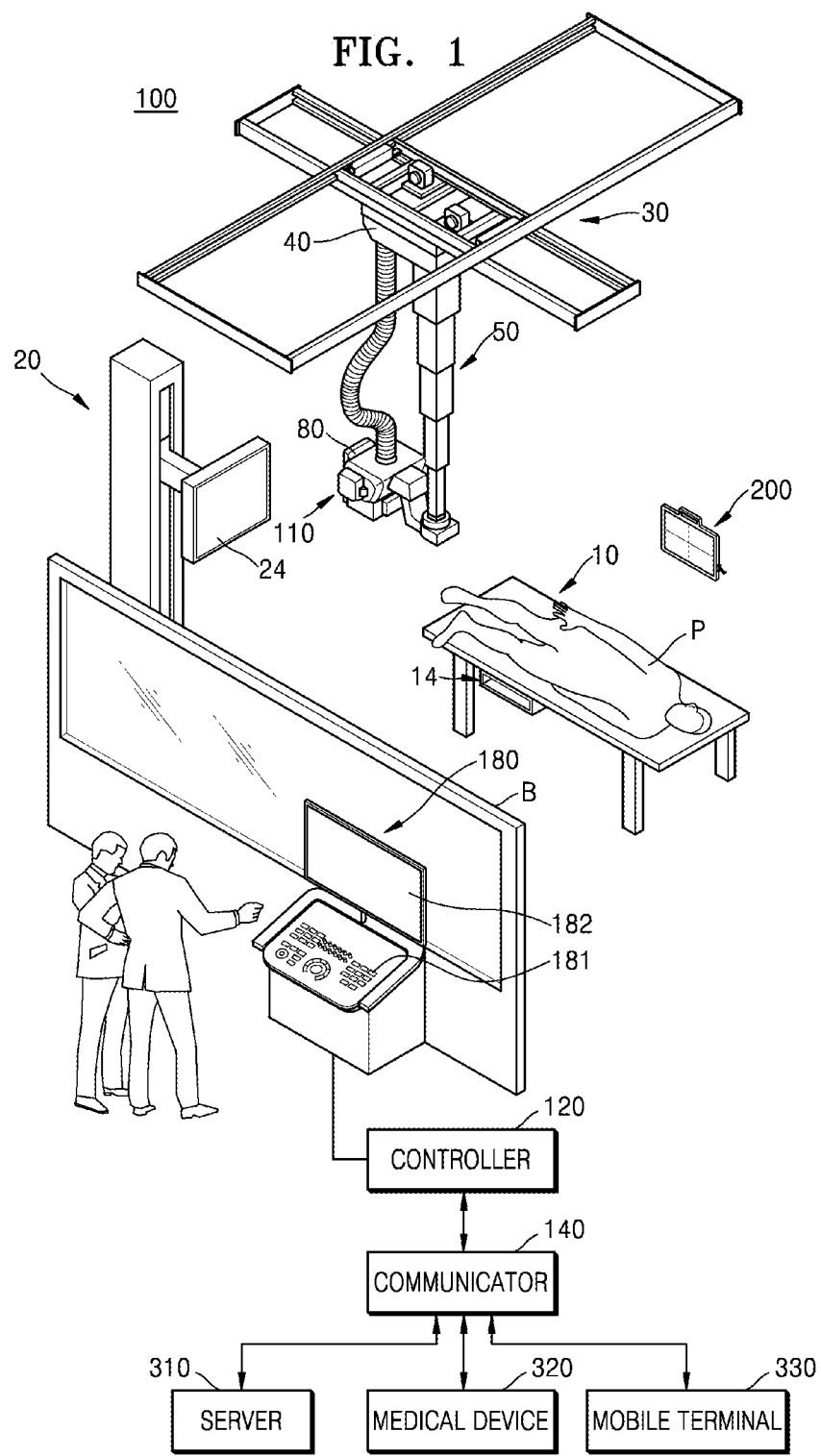
FIG. 1 illustrates a perspective diagram showing a configuration of an X-ray apparatus according to an embodiment of the present disclosure.

FIGS. 1 through 14, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. Expressions such as "at least one of," when preceding a list of elements, modify the entire list of elements and do not modify the individual elements of the list.

While the present disclosure will be particularly shown and described with reference to exemplary embodiments thereof, it is to be understood that the present disclosure is not limited to the disclosed embodiments, but, alternatively, is intended to cover various modifications and equivalent arrangements included within the spirit and scope of the present disclosure. The disclosed embodiments may be implemented in various forms.

Like reference numerals refer to like elements throughout the specification. This specification does not describe all the elements of the embodiments, and duplicate contents of the general contents or embodiments in the technical field of the present disclosure will be omitted. The terms "part" and "portion" as used herein may be embodied in software or hardware. According to embodiments, a plurality of "parts" or "portions" may be embodied as a single unit or a single element. Alternatively, a single 'part' or a single 'portion' may include a plurality of units or a plurality of elements. Hereinafter, the working principle and embodiments of the present disclosure will be described with reference to the accompanying drawings.

In the present specification, an image may include a medical image obtained by a medical scanning apparatus, such as a magnetic resonance photographing (MRI) apparatus, a computed tomography (CT) apparatus, an ultrasound photographing apparatus, or an X-ray photographing apparatus.

In this specification, an 'object' is an object of photography and may be a person, an animal, or a part thereof. For example, the object may include a part of the body (an internal organ) or a phantom.

FIG. 1 illustrates a perspective diagram showing a configuration of an X-ray apparatus 100 according to an embodiment of the present disclosure. The X-ray apparatus 100 of FIG. 1 is a fixed X-ray apparatus, as an example. However, the present disclosure is not limited thereto.

Referring to FIG. 1, the X-ray apparatus 100 may include an X-ray irradiator 110 for generating and irradiating an X-ray, an X-ray detector 200 for detecting an X-ray that is irradiated from the X-ray irradiator and transmitted through an object, and a workstation 180 that receives a command from a user and provides information to the user. The X-ray apparatus 100 may include a controller 120 for controlling the X-ray apparatus 100 according to an input command and a communicator 140 for communicating with an external apparatus.

Some or all of the components of the controller 120 and the communicator 140 may be included in the workstation 180 or provided separately from the workstation 180.

The X-ray irradiator 110 may include an X-ray source for generating an X-ray and a collimator for adjusting an irradiation area of the X-ray generated by the X-ray source.

A guide rail 30 may be installed on the ceiling of an examination room where the X-ray apparatus 100 is disposed. The X-ray irradiator 110 may be moved to a location corresponding to location of a target object P by connecting the X-ray irradiator 110 to a moving carriage 40 moving along the guide rail 30. The moving carriage 40 and the X-ray irradiator 110 may be connected to each other through a foldable post frame 50, such that the height of the X-ray irradiator 110 may be adjusted.

The workstation 180 may include an input unit 181 for receiving commands from a user and a display 182 for displaying information.

The input unit 181 may receive commands regarding a scanning protocol, scanning conditions, scanning timing, a position control of the X-ray irradiator 110, etc. The input unit 181 may include a keyboard, a mouse, a touch screen, a voice recognizer, etc.

The display 182 may display a screen image for guiding an input of a user, an X-ray image, a screen image showing the state of the X-ray apparatus 100, etc.

The controller 120 may control a scanning timing and scanning conditions of the X-ray irradiator 110 according to a command input from the user and may generate a medical image using image data received from the X-ray detector 200. Furthermore, the controller 120 may control the position or posture of mounts 14 and 24 to which the X-ray irradiator 110 or the X-ray detector 200 is mounted according to the scanning protocol and a position of the target object P.

The controller 120 may include a memory for storing a program for performing the above-described operation and other operations and a processor for executing the stored program. The controller 120 may include a single processor or a plurality of processors. In the latter example, a plurality of processors may be integrated on a single chip or may be physically separated from one another.

The X-ray apparatus 100 may be connected to an external device (e.g., an external server 310, a medical device 320, and a mobile terminal 330 (e.g., a smart phone, a tablet PC, a wearable device, etc.)) via the communicator 140 and transmit or receive data.

The communicator 140 may include at least one component that enables communication with an external device. For example, the communicator 140 may include at least one of a short-range communication module, a wired communication module, and a wireless communication module.

Furthermore, the communicator 140 may receive a control signal from an external device and transmit the received control signal to the controller 120, such that the controller 120 controls the X-ray apparatus 100 according to the received control signal.

Furthermore, the controller 120 may control an external device according to the control signal of the controller 120 by transmitting a control signal to the external device through the communicator 140. For example, the external device may process data of the external device according to the control signal of the controller 120 received via the communicator 140.

Furthermore, the communicator 140 may further include an internal communication module that enables communication among the components of the X-ray apparatus 100. Since a program for controlling the X-ray apparatus 100 may be installed on the external device, the program may include an instruction for performing some or all of the operations of the controller 120.

The program may be installed in the mobile terminal 330 in advance or the user of the mobile terminal 330 may download the program from the server that provides applications and install the program. The server providing applications may include a recording medium in which the program is stored.

The X-ray detector 200 may be a fixed X-ray detector fixed to a stand 20 or a table 10, may be detachably mounted to the mounts 14 and 24, or may be a portable X-ray detector that may be used at an arbitrary location. When the X-ray detector 200 is a portable X-ray detector, the X-ray detector 200 may be of a wire type or a wireless type depending on data transmission methods and power supply methods.

The X-ray detector 200 may be included as an element of the X-ray apparatus 100 or may not be included. In the latter example, the X-ray detector 200 may be registered to the X-ray apparatus 100 by a user. Furthermore, in both examples, the X-ray detector 200 may be connected to the controller 120 through the communicator 140 and receive a control signal or transmit image data.

A sub-user interface 80 for providing information to a user and receiving a command from a user may be provided at one end of the X-ray irradiator 110, where some or all of functions to be performed by the input unit 181 and the display 182 of the workstation 180 may be performed by the sub-user interface 80.

When all or some of the components of the controller 120 and the communicator 140 are provided separately from the workstation 180, the components may be included in the sub-user interface 80 provided in the X-ray irradiator 110.

Although FIG. 1 shows a fixed X-ray apparatus connected to the ceiling of an examination room, the X-ray apparatus 100 may have various structures within a range that is obvious to one of ordinary skill in the art, such as a C-arm type X-ray apparatus and a mobile X-ray apparatus.

Figure 2:
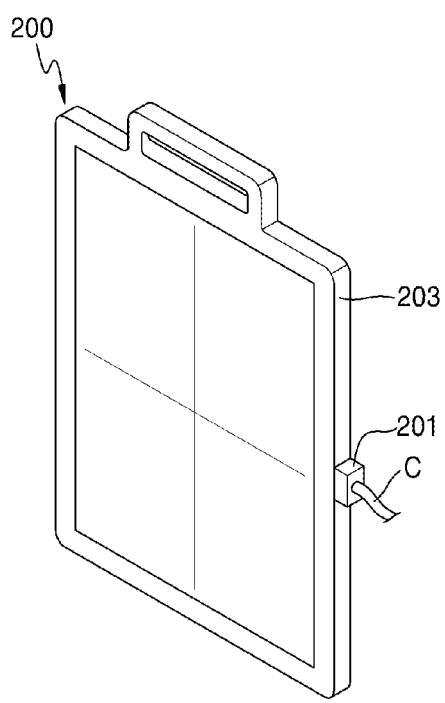
FIG. 2 illustrates a perspective view of a portable X-ray detector according to an embodiment of the present disclosure.

FIG. 2 illustrates a perspective view of a portable X-ray detector according to an embodiment of the present disclosure.

As described above, the X-ray detector 200 used in the X-ray apparatus 100 may be implemented as a portable X-ray detector. In this example, the X-ray detector 200 may include a battery for supplying power and operate wirelessly. Alternatively, as shown in FIG. 2, the X-ray detector 200 may operate as a charging port 201 is connected to a separate power supply unit by a cable C.

Inside a case 203 constituting the outer appearance of the X-ray detector 200, a detection element for detecting an X-ray and converting the X-ray into image data, a memory for temporarily or non-temporarily storing the image data, a communication module for receiving a control signal from the X-ray apparatus 100 or transmitting image data to the X-ray apparatus 100, and a battery may be provided. Furthermore, image correction information regarding the X-ray detector 200 and unique identification information regarding the X-ray detector 200 may be stored in the memory, and identification information stored during communication with the X-ray apparatus 100 may be transmitted together with the image correction information regarding the X-ray detector 200 and the unique identification information regarding the X-ray detector 200.

Figure 3:
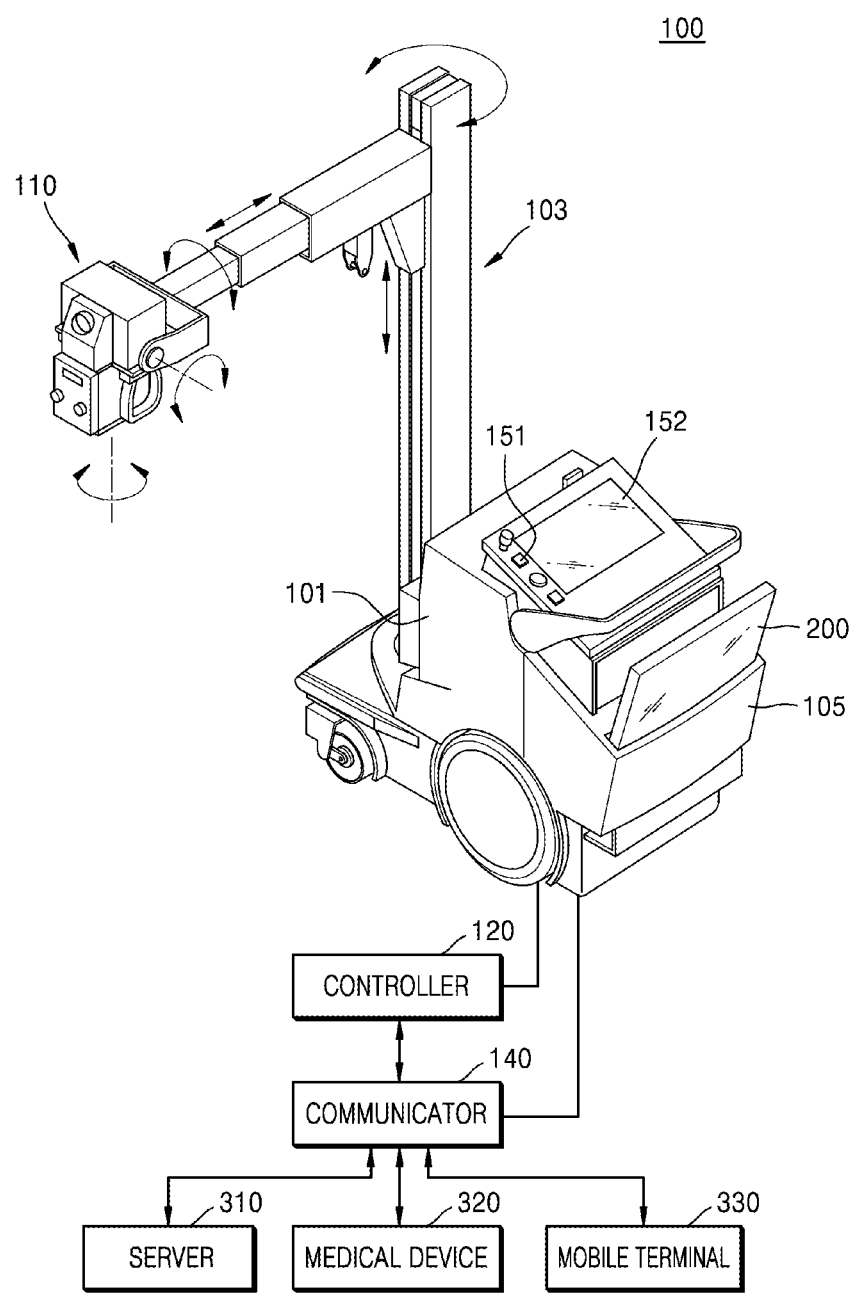
FIG. 3 illustrates a perspective view of a mobile X-ray apparatus according to an embodiment of the present disclosure.

FIG. 3 illustrates a perspective view of a mobile X-ray apparatus according to an embodiment of the present disclosure.

The same reference numerals as those in FIG. 1 denote the same functions, and thus redundant description of the reference numerals in FIG. 1 will be omitted.

An X-ray apparatus may be implemented not only as the ceiling type as described above, but also as a mobile type. When the X-ray apparatus 100 is implemented as a mobile X-ray apparatus, a main body 101 to which the X-ray irradiator 110 is connected may freely move and the an arm 103 interconnecting the X-ray irradiator 110 and the main body 101 may also be rotated and linearly move, and thus the X-ray irradiator 110 may freely move in the three-dimensional space.

The main body 101 may include a storage 105 for storing the X-ray detector 200. Furthermore, a charging terminal capable of charging the X-ray detector 200 is provided in the storage 105, such that the X-ray detector 200 may be stored while being charged.

An input unit 151, a display 152, the controller 120, and the communicator 140 may be provided in the main body 101. Image data obtained by the X-ray detector 200 may be transmitted to the main body 101 and displayed on the display 152 or transmitted to an external device through the communicator 140.

In one example embodiment, the controller 120 and the communicator 140 may be provided separately from the main body 101 and only some of the components of the controller 120 and the communicator 140 may be provided in the main body 101.

Figure 4:
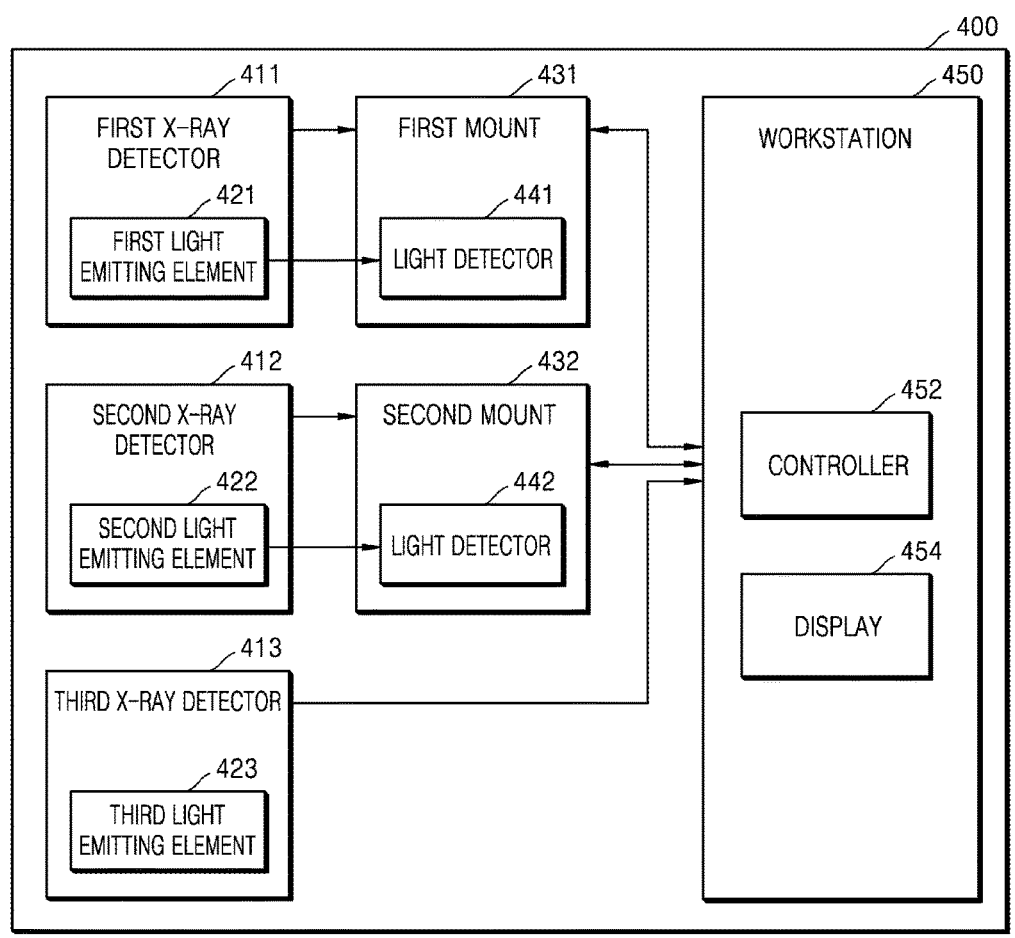
FIG. 4 illustrates a block diagram showing configuration of an X-ray apparatus according to an embodiment of the present disclosure.

FIG. 4 illustrates a block diagram showing configuration of an X-ray apparatus 400 according to an embodiment of the present disclosure.

Referring to FIG. 4, the X-ray apparatus 400 may include a plurality of X-ray detectors 411, 412, and 413, a plurality of mounts 431 and 432, and a workstation 450.

The plurality of X-ray detectors 411, 412, and 413 may include light emitting elements 421, 422, and 423, respectively. The first X-ray detector 411 may include a first light emitting element 421, the second X-ray detector 412 may include a second light emitting element 422, and the third X-ray detector 413 may include a third light emitting element 421. According to an embodiment of the present disclosure, the first light emitting element 421, the second light emitting element 422, and the third light emitting element 423 may include light emitting diodes (LED), but embodiments are not limited thereto.

According to an embodiment of the present disclosure, the first light emitting element 421, the second light emitting element 422, and the third light emitting element 423 may emit light of different colors. For example, the first light emitting element 421 may emit red light, the second light emitting element 422 may emit yellow light, and the third light emitting element 423 may emit blue light. According to an embodiment of the present disclosure, colors of the light emitted by the plurality of light emitting elements 421, 422, and 423 may be assigned by the workstation 450. Detailed descriptions thereof will be given below with reference to FIG. 9.

A plurality of X-ray detectors 411, 412, and 413 may be mounted to the plurality of mounts 431 and 432, respectively. According to an embodiment of the present disclosure, the first mount 431 may be a table-type mount, whereas the second mount 432 may be a stand-type mount. The table-type mount may be identical to the mount 14 of FIG. 1, whereas the stand-type mount may be identical to the mount 24 of FIG. 1.

The first X-ray detector 411 may be mounted to the first mount 431 and the second X-ray detector 412 may be mounted to the second mount 432. According to an embodiment of the present disclosure, the third X-ray detector 413 may be a portable X-ray detector that is not mounted to any mount. The third X-ray detector 413 may be implemented as a wired type or a wireless type according to data transmission methods and power supply methods.

The plurality of mounts 431 and 432 may include a plurality of light detectors 441 and 442, respectively. According to an embodiment of the present disclosure, the first mount 431 may include the plurality of light detectors 441, whereas the second mount 432 may include the plurality of light detectors 442. The plurality of light detectors 441 may sense the color of light emitted by the first light emitting element 421 included in the first X-ray detector 411 mounted to the first mount 431. In the same regard, the plurality of light detectors 442 may sense the intensity of light and color of light emitted by the second light emitting element 422 included in the second X-ray detector 412 mounted to the second mount 432.

According to an embodiment of the present disclosure, the plurality of mounts 431 and 432 may transmit information about the color of the light sensed by the plurality of light detectors 441 and 442 respectively included in of the mounts 431 and 432 to the workstation 450. According to an embodiment of the present disclosure, the third X-ray detector 413 is not mounted to the first mount 431 and the second mount 432 and may transmit identification information or positional information directly to the workstation 450. The identification information may include at least one of unique information including at least one of a MAC address and a serial number of the third X-ray detector 413 and specification information, such as size and dimension of the third X-ray detector 413.

According to an embodiment of the present disclosure, the plurality of light detectors 441 and 442 respectively included in the plurality of mounts 431 and 432 may sense the intensity of light emitted by the light emitting elements 421, 422, and 423. The plurality of mounts 431 and 432 may transmit information regarding the sensed intensity of the light to the workstation 450.

The workstation 450 may include a controller 452 and a display 454. The controller 452 may obtain positional information regarding the plurality of X-ray detectors 411 and 412 based on information on color of light received from the plurality of mounts 431 and 432. The controller 452 may also receive identification information and positional information from the third X-ray detector 413 and obtain positional information regarding the third X-ray detector 413 based on the received identification information and the received positional information. According to an embodiment of the present disclosure, the controller 452 may obtain at least one positional information from among the position of the first X-ray detector 411 mounted to the first mount 431, which is a table-type mount, the position of the second X-ray detector 411 mounted to the second mount 432, and the position of the third X-ray detector 413, which is not mounted to any one of the first mount 431 and the second mount 432.

According to an embodiment of the present disclosure, the controller 452 may be configured to include a memory for storing a program that implements an algorithm for obtaining positional information regarding the plurality of X-ray detectors 411, 412, 413 and a processor for executing the stored program. For example, the controller 452 may be implemented as at least one of a central processing unit (CPU), a graphic processing unit (GPU), and a microprocessor. According to an embodiment of the present disclosure, the controller 452 may be configured with hardware such as an FPGA or an ASIC.

The display 454 may display the positional information regarding the plurality of X-ray detectors 411, 412, and 413 in a user interface (UI) including at least one of letters, numbers, symbols, colors, and images. According to an embodiment of the present disclosure, the display 454 may display information indicating whether a particular X-ray detector from among the first through third X-ray detectors 411, 412, and 413 is mounted to the first mount 431 or the second mount 432 or is used as an unattached portable X-ray detector with an icon. According to an embodiment of the present disclosure, the display 454 may display information regarding a particular direction in which the particular X-ray detector is inserted to the mount with an icon.

The display 454 may include at least one of a CRT display, an LCD display, a PDP display, an OLED display, a FED display, an LED display, a VFD display, a digital light processing (DLP) display, a flat panel display, a 3D display, and a transparent display, but is not limited thereto.

During an X-ray scanning of a target object using the X-ray apparatus 400 including the plurality of X-ray detectors 411, 412, and 413, type of a mount to which an X-ray detector is to be mounted may differ according to scanning protocols, types of the target object, locations of the target object, etc. In this example, it is necessary for a user to check whether a particular one of the plurality of X-ray detectors 411, 412, and 413 is mounted to a particular mount, e.g., a table-type mount or a stand-type mount. Furthermore, the user may use a particular X-ray detector as a portable X-ray detector to photograph the object. The X-ray apparatus 400 according to an embodiment obtains positional information regarding the plurality of X-ray detectors 411, 412 and 413 and displays the positional information in the form of a user interface, and thus a user may intuitively grasp a particular mounted portion to which a particular X-ray detector is mounted or whether the particular X-ray detector is used as a portable X-ray detector. Therefore, the X-ray apparatus 400 according to an embodiment may improve user convenience and may prevent a false irradiation to a wrong X-ray detector or an over-irradiation.

Figure 5:
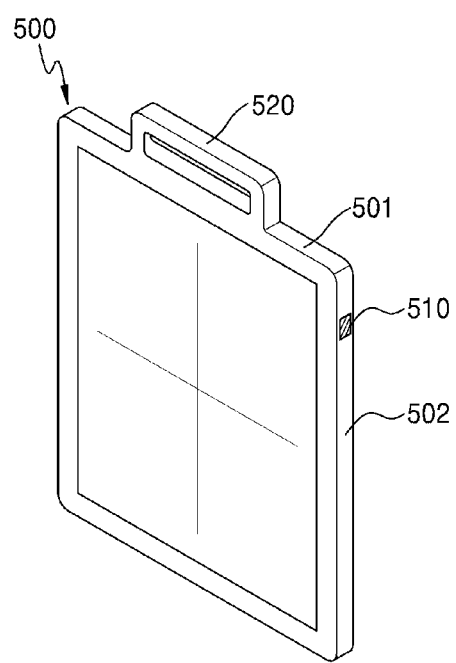
FIG. 5 illustrates a perspective view of an X-ray detector according to an embodiment of the present disclosure.

FIG. 5 illustrates a perspective view of an X-ray detector 500 according to an embodiment of the present disclosure.

Referring to FIG. 5, the X-ray detector 500 may be attached or detachably mounted to a stand 630 (i.e., stand-type mount) (see FIG. 6A) or a table—640 (i.e., table-type mount) (see FIG. 6B) or may also be implemented as a handheld X-ray detector that may be carried and used. The X-ray detector 500 may be implemented in a rectangular parallelepiped shape in which the length of a second surface 502 is greater than the length of a first surface 501. A light emitting element 510 may be disposed on a first side of the second surface 502 of the X-ray detector 500. Although FIG. 5 shows that the X-ray detector 500 includes a handle 520, the handle 520 is disposed on the first surface 501, and the light emitting element 510 is disposed on the second surface 502, it is merely an example. The light emitting element 510 may be disposed on any side surface of the X-ray detector 500 and is not limited to that shown in FIG. 5.

The light emitting element 510 may emit light of a particular color. According to an embodiment of the present disclosure, the light emitting element 510 may include a light emitting diode (LED), but is not limited thereto. For example, the light emitting element 510 may include a laser diode (LD) or a solid laser.

Figure 6A:
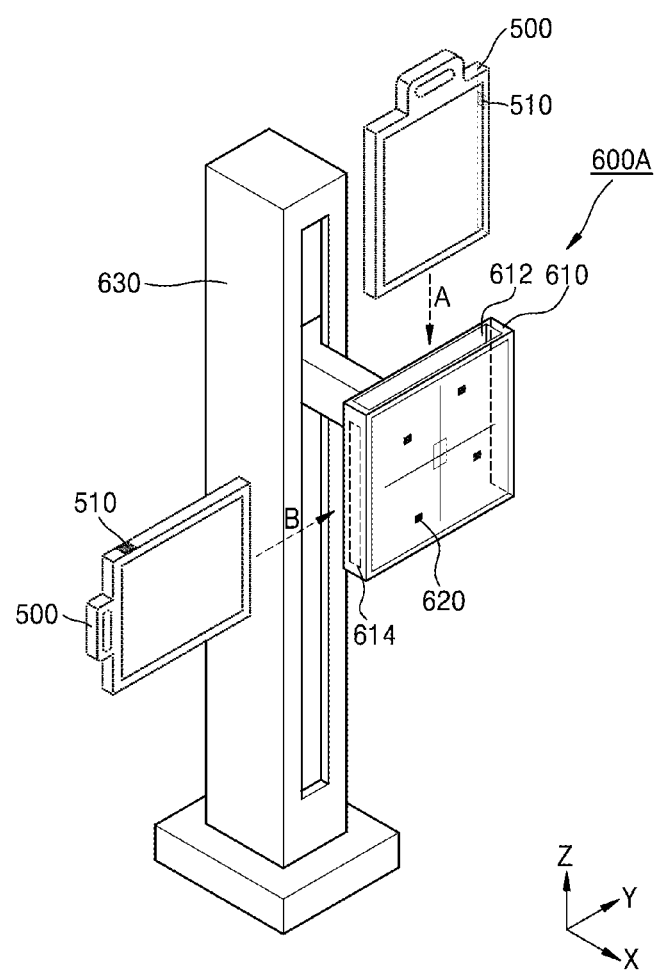
FIG. 6A illustrates a diagram for describing a method of mounting an X-ray detector according to an embodiment of the present disclosure to a stand-type mount.
Figure 6B:
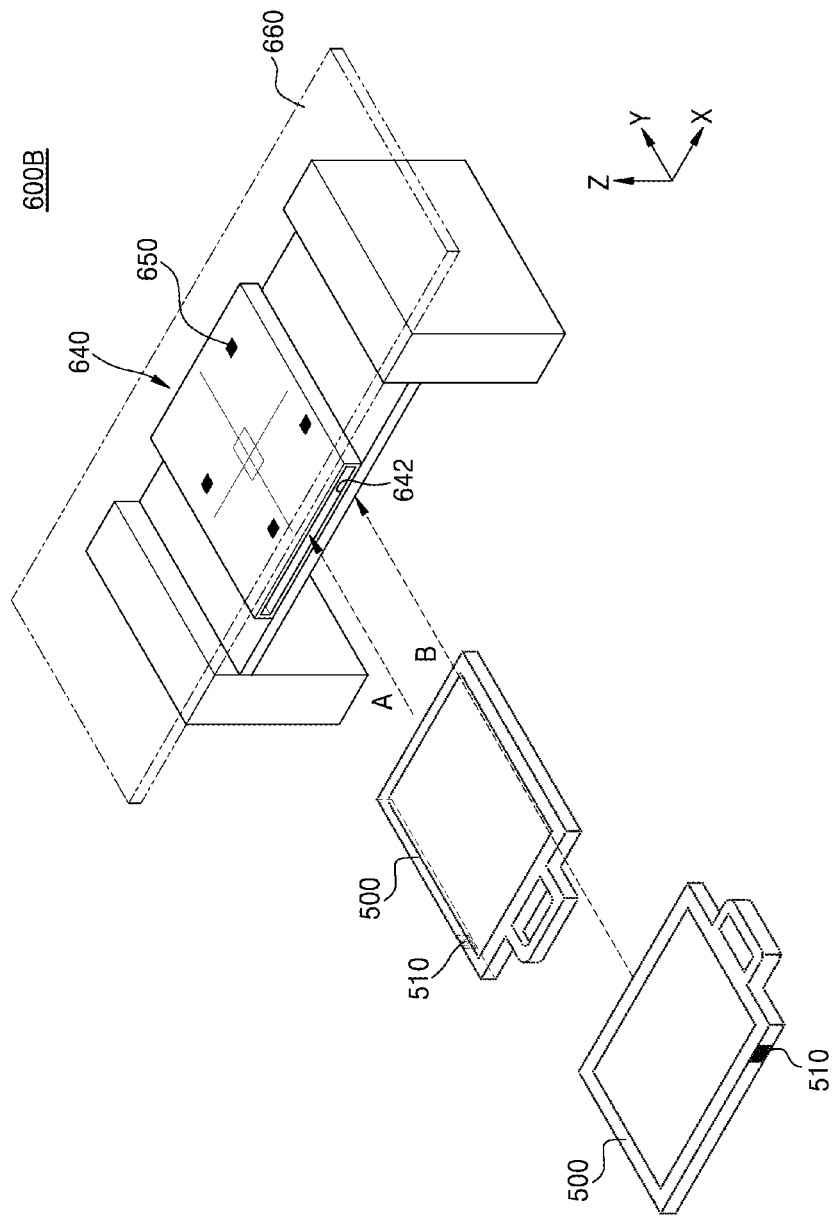
FIG. 6B illustrates a diagram for describing a method of mounting an X-ray detector according to an embodiment of the present disclosure to a table-type mount.

FIG. 6A illustrates a diagram for describing a method of mounting the X-ray detector 500 according to an embodiment to a stand-type mount 600A, and FIG. 6B illustrates a diagram for describing a method of mounting the X-ray detector 500 to a table-type mount 600B.

Referring to FIG. 6A, the stand-type mount 600A may include a mount 610, a plurality of light detectors 620, and a stand 630. According to an embodiment of the present disclosure, the stand-type mount 600A may further include a rail that may adjust position of the mount 610 in vertical directions along the z-axis.

The mount 610 may have a rectangular parallelepiped shape, a first insertion opening 612 may be disposed on the top surface of the mount 610, and a second insertion opening 614 may be disposed on the right side surface of the mount 610. The X-ray detector 500 may be inserted into the first insertion opening 612 (i.e., insertion port) in a portrait orientation in direction A along the Z-axis and coupled to the mount 610. Furthermore, the X-ray detector 500 may be inserted into the second insertion opening 614 in a landscape orientation in direction B along the Y-axis and coupled to the mount 610.

The plurality of light detectors 620 may be disposed on a surface facing the stand 630 from between the two largest surfaces of the mount 610. According to an embodiment of the present disclosure, the plurality of light detectors 620 may include the four light detectors 620. Any one of the plurality of light detectors 620 may be located at a position at which the corresponding light detectors 620 faces the light emitting element 510 disposed on a first side of the X-ray detector 500 mounted to the stand-type mount 600A. Detailed description thereof will be given below with reference to FIGS. 7A through 7D.

Referring to FIG. 6B, the table-type mount 600B may include a mount 640, a plurality of light detectors 650, and a table 660. According to an embodiment of the present disclosure, the table-type mount 600B may further include a rail capable of adjusting position of the mount 640 along the x-axis direction.

The mount 640 has a rectangular parallelepiped shape, and an insertion opening 642 may be disposed on the front surface. The X-ray detector 500 may be inserted in the direction A in the portrait orientation or in the direction B in the landscape orientation along the y-axis into the insertion opening 642 (i.e., insertion port) and coupled with the mount 640.

The plurality of light detectors 650 may be disposed apart from one another on the bottom surface of the mount 640. According to an embodiment of the present disclosure, the plurality of light detectors 650 may include the four light detectors 650. Any one of the plurality of light detectors 650 may be disposed at a location at which the corresponding light detector 650 faces the light emitting element 510 disposed at the first side of the X-ray detector 500 mounted to the table-type mount 600B.

Figure 7A:
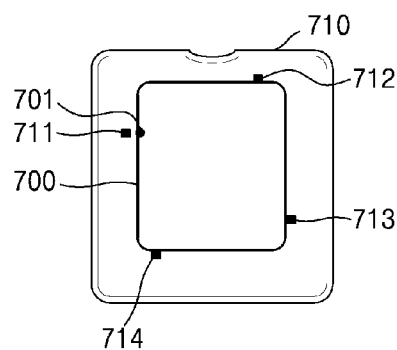
FIGS. 7A through 7D illustrate diagrams for describing a method for mounting an X-ray detector according to an embodiment of the present disclosure to a mount.
Figure 7B:
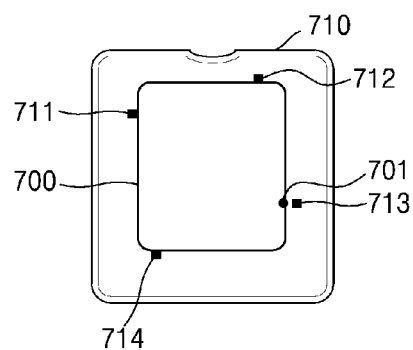
Figure 7C:
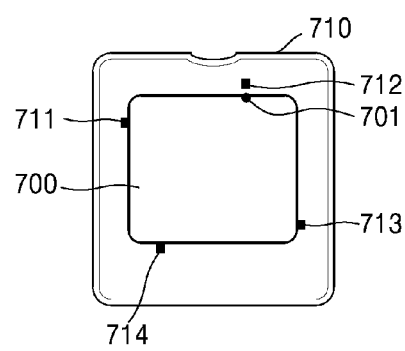
Figure 7D:
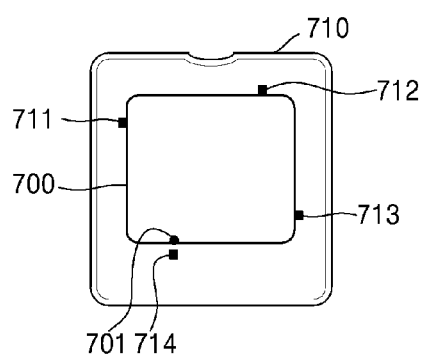

FIGS. 7A through 7D illustrate diagrams for describing a method for mounting an X-ray detector 700 according to an embodiment of the present disclosure to a mount 710. FIGS. 7A and 7B are diagrams showing a structure in which the X-ray detector 700 is inserted into the mount 710 in the direction A in the portrait orientation, and FIGS. 7C and 7D are diagrams showing the structure in which the X-ray detector 700 is inserted in the direction B in the landscape orientation. Referring to FIGS. 7A through 7D, a plurality of light detectors 711, 712, 713, and 714 may be included in the mount 710. The plurality of light detectors 711, 712, 713, and 714 may include the four light detectors 711, 712, 713, and 714 and may be disposed apart from one another.

According to an embodiment of the present disclosure, each of the plurality of light detectors 711, 712, 713, and 714 may include a light color sensor that detects the color of light emitted by the light emitting element 701. According to an embodiment of the present disclosure, each of the plurality of light detectors 711, 712, 713, and 714 may further include a light intensity sensor that detects an intensity of light emitted by the light emitting element 701.

Referring to FIG. 7A, the X-ray detector 700 may be inserted into the mount 710 in the direction A in the portrait orientation. The light emitting element 701 may be disposed at the first side of the X-ray detector 700. The light emitting element 701 may be arranged to face the first light detector 711 according to the direction in which the X-ray detector 700 is inserted into the mount 710. According to an embodiment of the present disclosure, the first light detector 711 may sense color of light emitted by the light emitting element 701. The first light detector 711 may recognize the X-ray detector 700 mounted to the mount 710 based on the sensed color of the light.

Furthermore, according to an embodiment of the present disclosure, the first light detector 711 from among the plurality of light detectors 711, 712, 713, and 714 may sense intensity of light emitted by the light emitting element 701, whereas the second through fourth light detectors 712 through 714 may not be able to sense an intensity of light or may only be able to detect very weak light. Therefore, the plurality of light detectors 711, 712, 713, and 714 may recognize a direction in which the X-ray detector 700 is inserted into the mount 710. In FIG. 7A, the X-ray detector 700 may be inserted into the mount 710 in the direction A in the portrait orientation.

In the embodiment shown in FIG. 7B, the X-ray detector 700 is inserted into the mount 710 in the direction A in the portrait orientation as shown in FIG. 7A. However, unlike in FIG. 7A, the X-ray detector 700 may be turned upside down and inserted into the mount 710. In this example, the light emitting element 701 disposed at the first side of the X-ray detector 700 may be located to face the third light detector 713 from among the plurality of light detectors 711, 712, 713, and 714. According to an embodiment of the present disclosure, the third light detector 713 may sense color of light emitted by the light emitting element 701. The third light detector 713 may recognize the X-ray detector 700 mounted to the mount 710 based on the sensed color of the light.

The third light detector 713 from among the plurality of light detectors 711, 712, 713 and 714 may senses intensity of light emitted by the light emitting element 701, whereas the first light detector 711, the second light detector 712, and the fourth light detector 714 may not be able to sense intensity of light or may only detect very weak light. Therefore, the plurality of light detectors 711, 712, 713, and 714 may recognize a direction in which the X-ray detector 700 is inserted into the mount 710.

In the embodiment shown in FIG. 7C, the X-ray detector 700 is inserted into the mount 710 in the direction B in the landscape orientation. The light emitting element 701 disposed at the first side of the X-ray detector 700 may be located to face the second light detector 712 from among the plurality of light detectors 711, 712, 713, and 714. According to an embodiment of the present disclosure, the second light detector 712 may sense color of light emitted by the light emitting element 701. The second light detector 712 may recognize the X-ray detector 700 mounted to the mount 710 based on the sensed color of the light.

Furthermore, according to an embodiment of the present disclosure, the plurality of light detectors 711, 712, 713, and 714 may recognize a direction in which the X-ray detector 700 is inserted into the mount 710. The method by which the plurality of light detectors 711, 712, 713, and 714 recognize a direction in which the X-ray detector 700 is inserted into the mount 710 is identical to the method described above with reference to FIGS. 7A and 7B, detailed description thereof will be omitted.

In the embodiment shown in FIG. 7D, the X-ray detector 700 is inserted in the direction B in the landscape orientation into the mount 710. The light emitting element 701 disposed at the first side of the X-ray detector 700 may be located to face the fourth light detector 714 from among the plurality of light detectors 711, 712, 713, and 714. According to an embodiment of the present disclosure, the fourth light detector 714 may sense color of light emitted by the light emitting element 701. The fourth light detector 714 may recognize the X-ray detector 700 mounted to the mount 710 based on the sensed color of the light.

Furthermore, according to an embodiment of the present disclosure, the plurality of light detectors 711, 712, 713, and 714 may recognize a direction in which the X-ray detector 700 is inserted into the mount 710. The method by which the plurality of light detectors 711, 712, 713, and 714 recognize a direction in which the X-ray detector 700 is inserted into the mount 710 is identical to the method described above with reference to FIGS. 7A and 7B, detailed description thereof will be omitted.

Figure 8:
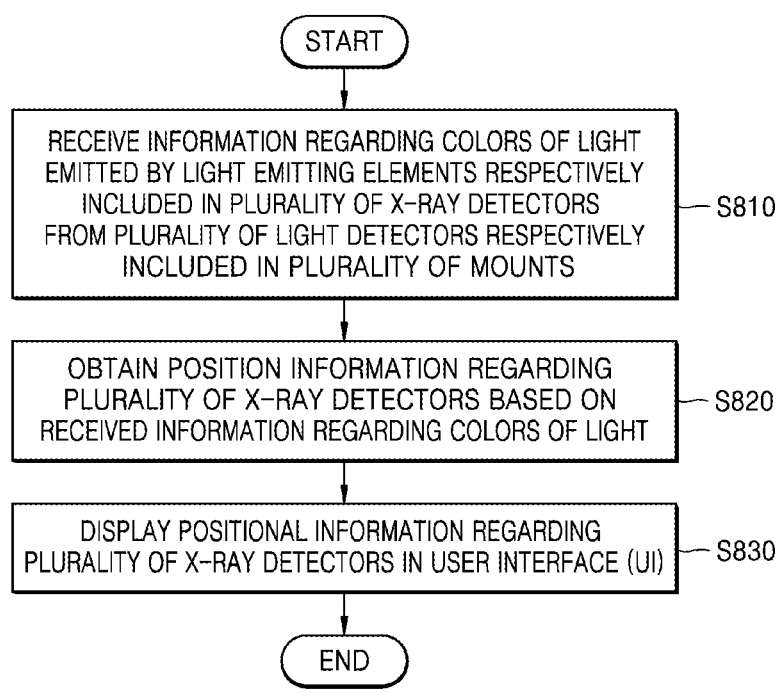
FIG. 8 illustrates a method of providing positional information regarding a plurality of X-ray detectors according to an embodiment of the present disclosure.

FIG. 8 illustrates a method of providing positional information regarding a plurality of X-ray detectors according to an embodiment of the present disclosure.

In operation S810, an X-ray apparatus receives color information regarding light emitted by light emitting elements included in a plurality of X-ray detectors from a plurality of light detectors included in the plurality of mounts, respectively. The light emitting elements may emit light of different colors according to the plurality of X-ray detectors including the light emitting elements. According to an embodiment of the present disclosure, the X-ray apparatus may include a workstation. The plurality of light detectors may sense colors of light emitted by the light emitting elements, and the plurality of mounts may transmit information regarding the colors of the light sensed by the light detector to the workstation.

According to an embodiment of the present disclosure, the plurality of mounts may include stand-type mounts or table-type mounts. According to an embodiment of the present disclosure, a portable X-ray detector may not be mounted to any of the stand-type mounts and the table-type mounts. In this example, the workstation may receive positional information from the portable X-ray detector.

In operation S820, the X-ray apparatus obtains positional information regarding the plurality of X-ray detectors based on the color information regarding light. According to an embodiment of the present disclosure, the workstation included in the X-ray apparatus may receive color information regarding light emitted by the light emitting elements of the X-ray detector from the plurality of mounts. According to an embodiment of the present disclosure, the workstation may obtain positional information related to the coupling of the first X-ray detector with the stand-type mount or the coupling of the second X-ray detector with the table-type mount. Furthermore, the workstation may directly obtain positional information regarding the third X-ray detector from the third X-ray detector operating as a portable X-ray detector.

According to an embodiment of the present disclosure, the workstation may sense a direction in which the first X-ray detector is mounted to the stand-type mount based on intensity of light received by the light detector that is located to face the first side of the first type X-ray detector mounted to the stand-type mount. In the same regard, the workstation may obtain information regarding a direction in which the second X-ray detector is mounted to the table-type mount based on intensity of light received by the light detector that is located to face the first side of the second type X-ray detector mounted to the table-type mount.

In operation S830, the X-ray apparatus displays positional information regarding the plurality of X-ray detectors in the form of a user interface (UI). According to an embodiment of the present disclosure, the X-ray apparatus may include a display, and the display may display positional information regarding the plurality of X-ray detectors in the form of a UI including at least one of letters, numbers, symbols, colors, and images. According to an embodiment of the present disclosure, the workstation may display information regarding directions in which the plurality of X-ray detectors is mounted to the plurality of mounts in the form of a UI.

Figure 9:
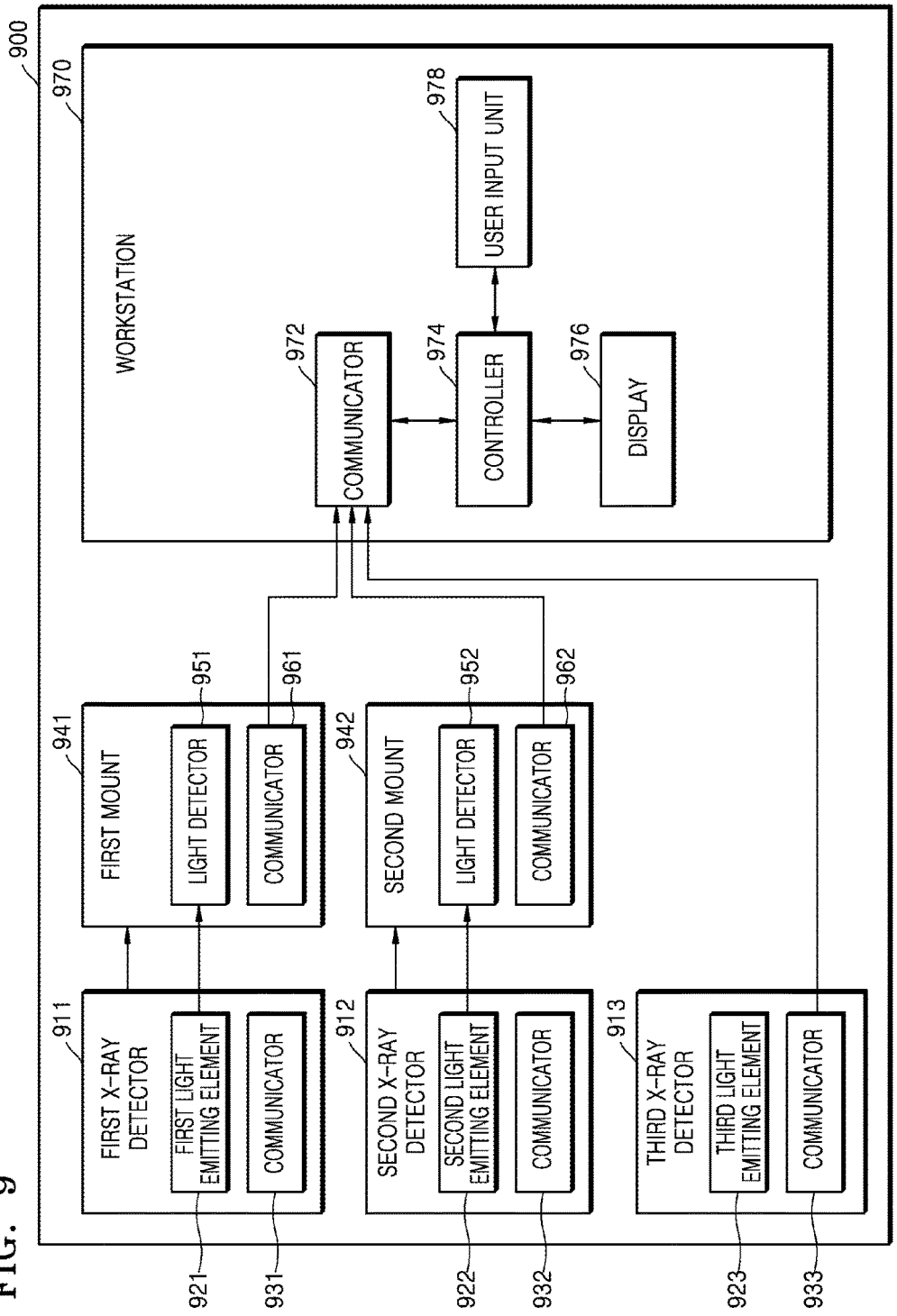
FIG. 9 illustrates a block diagram showing the configuration of an X-ray apparatus according to an embodiment of the present disclosure.

FIG. 9 illustrates a block diagram showing the configuration of an X-ray apparatus 900 according to an embodiment of the present disclosure.

Referring to FIG. 9, the X-ray apparatus 900 may include a plurality of X-ray detectors 911, 912, and 913, a plurality of mounts 941 and 942, and a workstation 970. The plurality of X-ray detectors 911, 912 and 913 may be identical to the plurality of X-ray detectors 411, 412 and 413 shown in FIG. 4, and the plurality of mounts 941 and 942 may be identical to the plurality of the mounts 431 shown in FIG. 4. Therefore, redundant descriptions of the plurality of X-ray detectors 911, 912, and 913 and the plurality of mounts 941 and 942 will be omitted, descriptions below will focus on differences between the plurality of X-ray detectors 911, 912, and 913 and the plurality of X-ray detectors 411, 412, and 413 and differences between the plurality of mounts 941 and 942 and the plurality of mounts 431 and 432 shown in FIG. 4.

The plurality of X-ray detectors 911, 912, and 913 may include light emitting elements 921, 922, and 923 and communicators 931, 932, and 933, respectively. The communicators 931, 932, and 933 may transmit identification information regarding the plurality of X-ray detectors 911, 912, and 913 to the workstation 970. Each of the communicators 931, 932, and 933 may include one or more components that enable communication with an external device and the workstation 970. For example, each of the communicators 931, 932, and 933 may include at least one of a short-range communication module, a wired communication module, and a wireless communication module. For example, the identification information may include unique information including at least one of a MAC address, an internet protocol (IP) address, and a serial number of each of a plurality of X-ray detectors 911, 912 and 913 and specification information including at least one of information regarding respective sizes of the plurality of X-ray detectors 911, 912, and 913 and information regarding types of mounts to which the plurality of X-ray detectors 911, 912, and 913 may be mounted. According to an embodiment of the present disclosure, the communicators 931, 932, and 933 may transmit positional information regarding the plurality of X-ray detectors 911, 912, and 913 to the workstation 970 in addition to the unique information and the specification information.

For example, the communicator 931 included in the first X-ray detector 911 may transmit identification information including the MAC address or the IP address of the first X-ray detector 911 to the workstation 970. The communicator 933 included in the third X-ray detector 913, which is not mounted in any one of the first mount 941 and the second mount 942, may transmit the identification information and the positional information regarding the third X-ray detector 913 to the workstation 970.

According to an embodiment of the present disclosure, the communicators 931, 932, and 933 may receive information regarding colors of light respectively assigned to the plurality of X-ray detectors 911, 912, and 913 from the workstation 970.

Communicators 961 and 962 respectively included in the plurality of mounts 941 and 942 may transmit information regarding colors of light sensed by the light detectors 951 and 952 to the workstation 970. In an embodiment, the light detector 951 included in the first mount 941 may detect color of light emitted by the first light emitting element 921 of the first X-ray detector 911 mounted to the first mount 941, and the communicator 961 may transmit information regarding the sensed color of the light to a communicator 972 of the workstation 970. In the same regard, the light detector 952 included in the second mount 942 may sense color of light emitted by the first light emitting element 922 of the second X-ray detector 912 mounted to the second mount 942, and the controller 974 may transmit information regarding the sensed color of the light to the communicator 972 of the workstation 970.

The workstation 970 may include the communicator 972, a controller 974, a display 976, and a user input unit 978.

The communicator 972 may receive identification information regarding each of the plurality of X-ray detectors 911, 912, and 913 from the communicators 931, 932, and 933 respectively included in the plurality of X-ray detectors 911, 912, and 913. Furthermore, the communicator 972 may receive information regarding colors of light sensed by the light detectors 951 and 952 included in the plurality of mounts 941 and 942 from the communicators 961 and 962 included in the plurality of mounts 941 and 942. The communicator 972 may include one or more components capable of transmitting and receiving data via a wire or wirelessly with the plurality of X-ray detectors 911, 912, and 913 and the plurality of mounts 941 and 942. For example, the communicator 972 may perform data communication with the plurality of X-ray detectors 911, 912, and 913 and the plurality of mounts 941 and 942 by using at least one of a communication techniques including wireless LAN, Wi-Fi, Bluetooth, ZigBee, Wi-Fi Direct, infrared data association (IrDA), Bluetooth low energy (BLE), near field communication (NFC), wireless broadband internet (WiBro), world interoperability for microwave access (WiMAX), shared wireless access protocol (SWAP), wireless gigabit alliance (WiGig), and a RF communication technique. However, the present disclosure is not limited thereto.

Since the controller 974 is identical to the controller 452 shown in FIG. 4, detailed description thereof will be omitted. However, in the embodiment shown in FIG. 9, the controller 974 may assign different colors of light to the plurality of X-ray detectors 911, 912, and 913 based on identification information regarding the plurality of X-ray detectors 911, 912, and 913 received by the communicator 972, respectively. For example, the controller 974 may assign red light to the identification information regarding the first X-ray detector 911, assign yellow light to the identification information regarding the second X-ray detector 912, and assign blue light to the identification information regarding the third X-ray detector 913. According to an embodiment of the present disclosure, the communicator 972 may transmit information regarding assigned colors of light to the communicators 931, 932, and 933 included in the plurality of X-ray detectors 911, 912, and 913, respectively.

The display 976 may display positional information regarding each of the plurality of X-ray detectors 911, 912 and 913 obtained by the controller 974 in the form of a user interface including at least one of letters, numbers, symbols, colors, and images. Since the display 976 is identical to the display 454 shown in FIG. 4, detailed description thereof will be omitted.

The user input unit 978 may receive a user input for selecting an scan mode for performing X-ray scanning by using a stand-type mount, a table-type mount, and a portable-type (not coupled with a mount). The user input unit 978 may include at least one of a control panel, a trackball, a mouse, and a keyboard, but is not limited thereto According to an embodiment of the present disclosure; the user input unit 978 may be configured in the form of a touch screen coupled with the display 976. When the user input unit 978 is configured as a touch screen, scan mode user interfaces corresponding to a stand-type mount, a table-type mount, and a portable-type is displayed on the touch screen, and the user input unit 978 may receive a touch input of a user who selects any one of displayed scan mode user interfaces.

According to an embodiment of the present disclosure, the controller 974 may determine where any one of the plurality of X-ray detectors 911, 912, and 913 is mounted to a mount corresponding to a scan mode selected by a user input received by the user input unit 978 and determine whether an X-ray scanning may be performed according to the selected scan mode and the determination of whether a corresponding X-ray detector is mounted. Detailed description thereof will be given below with reference to FIG. 10. According to an embodiment of the present disclosure, the display 976 may display information determined by the controller 974 regarding whether an X-ray scanning may be performed in the form of a user interface.

A user who uses the X-ray apparatus 900 may set different X-ray scan modes according to scan protocols or types and locations of a target object. For example, an X-ray scanning may be performed by mounting an X-ray detector to a stand-type mount, an X-ray scanning may be performed by mounting an X-ray detector to a table-type mount, or an X-ray scanning may be performed by using an X-ray detector as a portable X-ray detector without mounting the same to any mount. The X-ray apparatus 900 according to an embodiment may receive a user input for selecting an scan mode for X-ray scanning and, according to the selected scan mode, provides an intuitive user interface indicating a particular mount having mounted thereon a corresponding X-ray detector or, when the corresponding X-ray detector operates as a portable X-ray detector, location of the portable X-ray detector, thereby improving user convenience.

Figure 10:
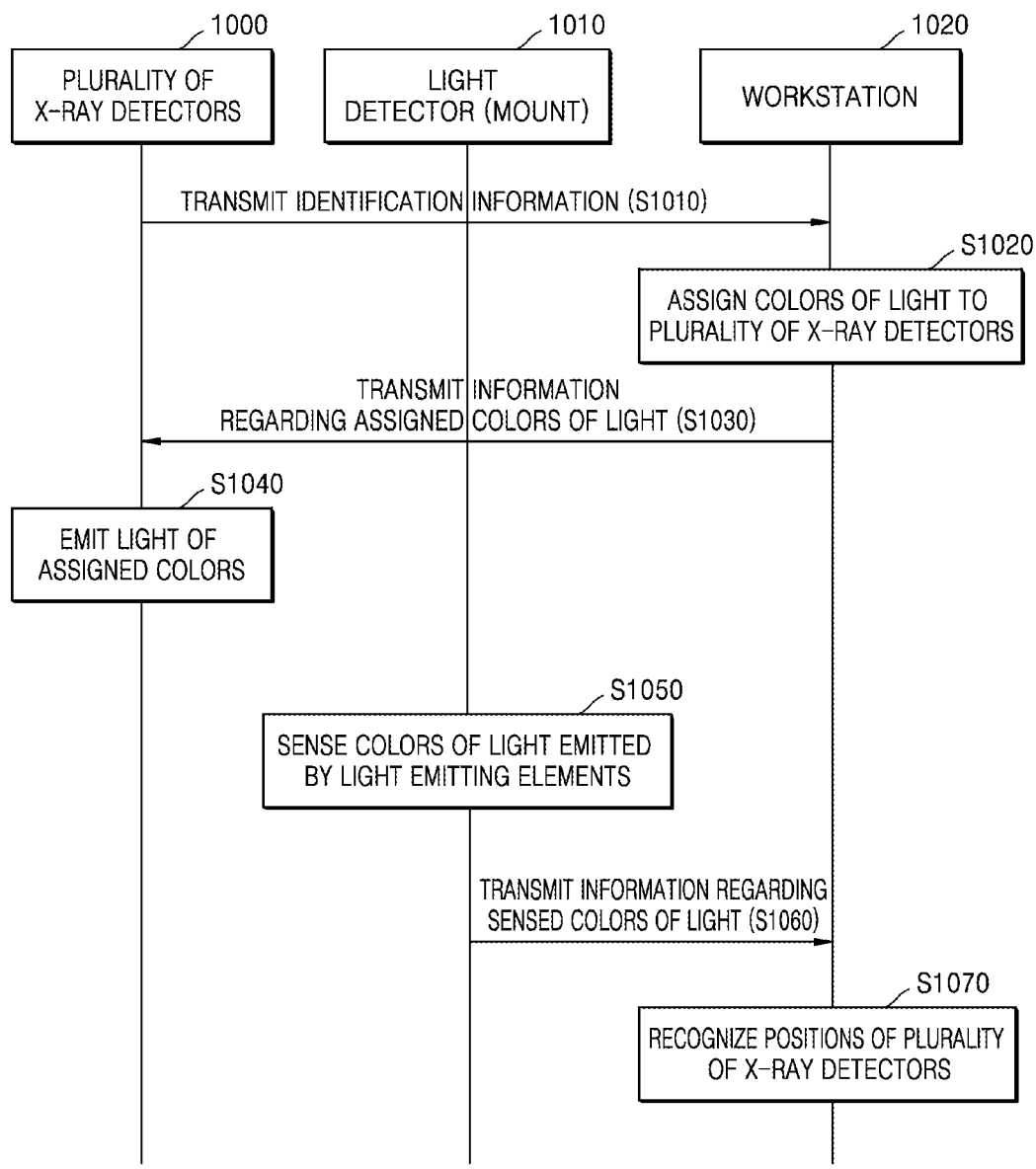
FIG. 10 illustrates a method used by an X-ray apparatus according to an embodiment to provide positional information regarding a plurality of X-ray detectors.

FIG. 10 illustrates a method by which an X-ray apparatus according to an embodiment provides positional information regarding a plurality of X-ray detectors. The X-ray apparatus may include a plurality of X-ray detectors 1000, a light receiving element 1010 included in a mount, and a workstation 1020.

In operation S1010, the plurality of X-ray detectors 1000 transmit identification information to the workstation 1020. According to an embodiment of the present disclosure, the plurality of X-ray detectors 1000 may transmit identification information regarding each of the plurality of the X-ray detectors 1000, e.g., at least one of a MAC address, an IP address, and a serial number, to the workstation 1020. Furthermore, the plurality of X-ray detectors 1000 may transmit information regarding size of each of the plurality of X-ray detectors 1000 and information regarding types of mounts to which the plurality of X-ray detectors 1000 may be mounted, to the workstation 1020.

In operation S1020, the workstation 1020 allocates different light colors to the plurality of X-ray detectors 1000, respectively. According to an embodiment of the present disclosure, the workstation 1020 may assign different light colors to the plurality of X-ray detectors 1000 according to identification information received from the plurality of X-ray detectors 1000, respectively.

In operation S1030, the workstation 1020 transmits information on the allocated light colors to the plurality of X-ray detectors 1000, respectively.

In operation S1040, the plurality of X-ray detectors 1000 emit light of the assigned colors. According to an embodiment of the present disclosure, light emitting elements included in the plurality of X-ray detectors 1000 may emit light of different colors.

In operation S1050, the light receiving element 1010 detects colors of light emitted by the light emitting elements respectively included in the plurality of X-ray detectors 1000. According to an embodiment of the present disclosure, each light receiving element 1010 may include a light color sensing sensor that senses the color of light emitted by the light emitting element.

In operation S1060, the mount including the light receiving element 1010 transmits information regarding color of sensed light to the workstation 1020. According to an embodiment of the present disclosure, the mount may include communicators 961 and 962 (refer to FIG. 9) as well as the light receiving element 1010, and the communicators 961 and 962 may transmit information regarding colors of light sensed by the light detector 1010 to the workstation 1020.

In operation S1070, the workstation 1020 recognizes positions of the plurality of X-ray detectors 1000. According to an embodiment of the present disclosure, the workstation 1020 may obtain positional information regarding a particular mount to which a particular one of the plurality of X-ray detectors 1000 is mounted or the particular one of the plurality of X-ray detectors 1000 is used as a portable X-ray detector without being mounted to any mount. According to an embodiment of the present disclosure, the workstation 1020 may recognize directions in which the plurality of X-ray detectors 1000 is mounted to the mount, respectively.

Figure 11A:
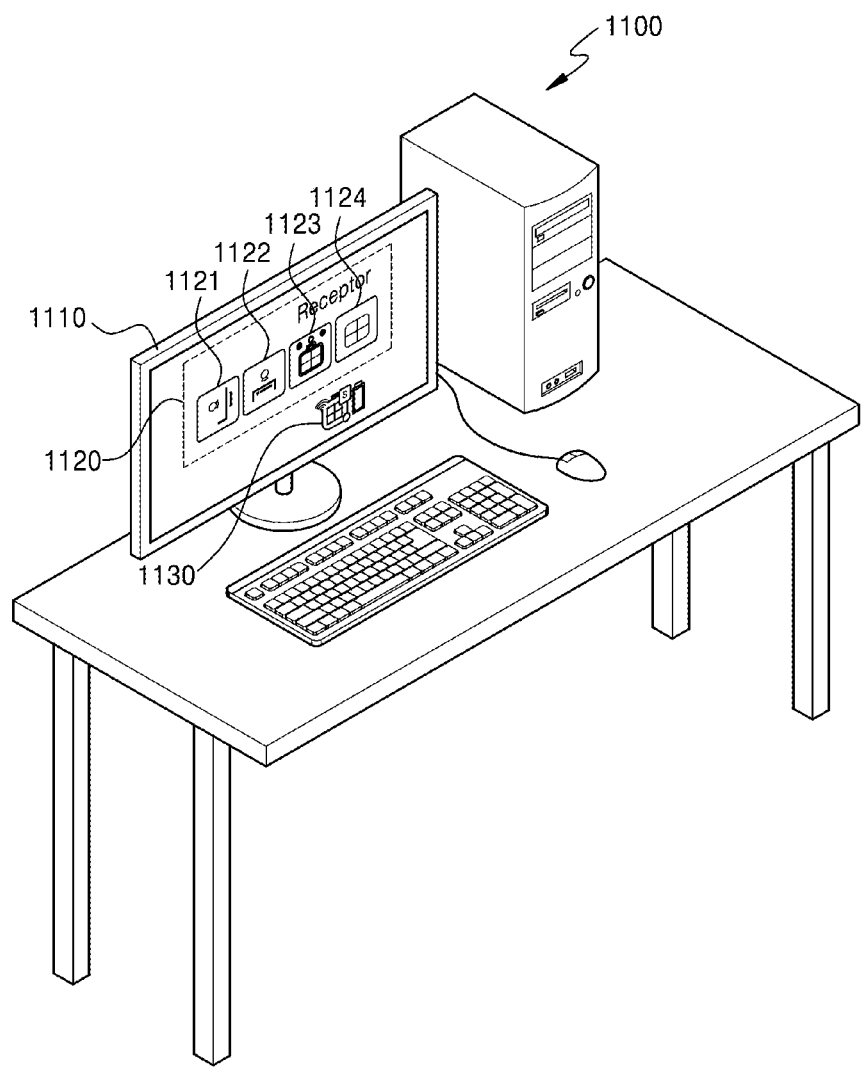
FIG. 11A illustrates a diagram showing a workstation according to an embodiment of the present disclosure.
Figure 11B:
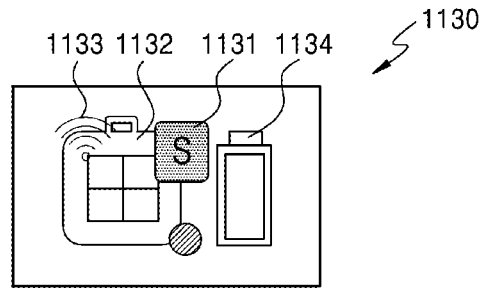
FIG. 11B illustrates a diagram showing a user interface via which the workstation shown in FIG. 11A displays positional information regarding a plurality of X-ray detectors.

FIG. 11A illustrates a diagram showing a workstation 1100 according to an embodiment of the present disclosure, and FIG. 11B illustrates a diagram showing a user interface via which the workstation 1100 shown in FIG. 11A displays positional information regarding a plurality of X-ray detectors and information regarding directions in which the plurality of X-ray detectors are mounted to a plurality of mounts.

Referring to FIG. 11A, the workstation 1100 includes a display 1110, and scan mode icons 1120 for receiving a user input for selecting a scan mode and a status information icon 1130 regarding an X-ray detector may be displayed on the display 1110.

The scan mode icons 1120 may include a stand-type scanning icon 1121, a table-type scanning icon 1122, a portable-type scanning icon 1123, and a mounted direction icon 1124. When a user selects the stand-type scanning icon 1121, the X-ray apparatus may recognize whether an X-ray detector is mounted to a stand-type mount and determine whether X-ray scanning may be performed according to the scanning mode selected by the user. According to another embodiment of the present disclosure, when the user selects the stand-type scanning icon 1121, the X-ray apparatus may activate an X-ray detector such that the X-ray detector may be mounted to a stand-type mount and used for X-ray scanning. Similarly, when a user input for selecting the table-type scanning icon 1122 is received, the X-ray apparatus may recognize whether an X-ray detector is mounted to a table-type mount and may determine whether X-ray scanning may be performed according to the table-type scan mode selected by the user. When a user input for selecting the portable-type scanning icon 1123 is received, the X-ray apparatus may recognize whether the X-ray detector is operated as a portable X-ray detector without being mounted to any of the stand-type mount and the table-type mount and determine whether X-ray scanning may be performed according to the portable-type scan mode selected by the user. The mounted direction icon 1124 may display information regarding a direction in which an X-ray detector is mounted when the X-ray detector is mounted to the stand-type mount or the table-type mount.

The status information icon 1130 regarding an X-ray detector may be displayed on a taskbar of the display 1110. The status information icon 1130 regarding an X-ray detector may display color of light emitted by a light emitting element included in a corresponding X-ray detector and current positional information regarding the corresponding X-ray detector. The status information icon 1130 may also display identification information regarding the corresponding X-ray detector and information regarding a current status of the corresponding X-ray detector.

Referring to FIG. 11B, the status information icon 1130 regarding an X-ray detector includes a first icon 1131 for displaying positional information regarding a corresponding X-ray detector and color of light emitted by the corresponding X-ray detector, a second icon 1132 indicating that the corresponding X-ray detector is a wireless detector, a third icon 1133 indicating information regarding communication sensitivity of the corresponding X-ray detector, and a fourth icon 1134 indicating information regarding remaining battery level of the corresponding X-ray detector.

The first icon 1131 may display positional information regarding an X-ray detector and color of light emitted by a light emitting element included in the X-ray detector. For example, referring to FIG. 11B, the first icon 1131 may display a letter "S" indicating that a current X-ray detector is mounted to a stand-type mount on a red background indicating that a light emitting element included in the current X-ray detector emits red light. According to another embodiment of the present disclosure, the first icon 1131 may display a letter "T" indicating that a current X-ray detector is mounted to a table-type mount on a yellow background indicating that a light emitting element included in the current X-ray detector emits yellow light. When the X-ray detector is not mounted to any of the stand-type mount and the table-type mount and is operated as a portable X-ray detector, the first icon 1131 may display the letter "P".

The second icon 1132, the third icon 1133, and the fourth icon 1134 may be displayed as sub icons indicating current states of an X-ray detector.

In the embodiment shown in FIGS. 11A and 11B, the X-ray apparatus may display the status information icon 1130 regarding an X-ray detector on the display 1110 of the workstation 1100. Therefore, since a user may simply rapidly refer to positional information regarding the X-ray detector, color of light emitted by the X-ray detector, and the state information regarding the X-ray detector, the X-ray detector may be managed and controlled more efficiently.

FIGS. 12A through 12D illustrate diagrams for describing a method by which an X-ray detector according to an embodiment determines whether X-ray scanning may be performed according to a scan mode selected based on a user input.

Figure 12A:
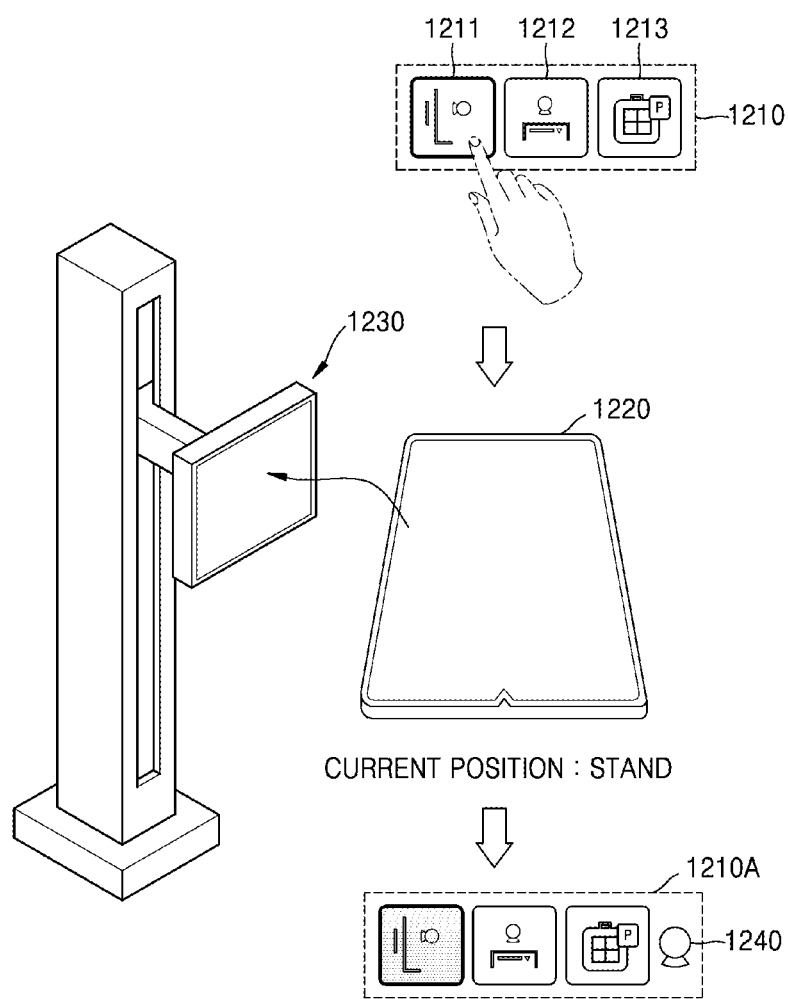
FIGS. 12A through 12D illustrate diagrams for describing a method used by an X-ray detector according to an embodiment to determine whether X-ray scanning may be performed according to a scan mode selected based on a user input.

Referring to FIG. 12A, the X-ray apparatus may display a user interface 1210 including a stand-type scan mode icon 1211, a table-type scan mode icon 1212, and a portable-type scan mode icon 1213 and may receive a user input for selecting any one of a stand-up type scan mode, a table-type scan mode, and a portable-type scan mode via the user interface 1210. In the embodiment shown in FIG. 12A, the X-ray apparatus may receive a user input for selecting the stand-type scan mode icon 1211. The X-ray apparatus may determine whether an X-ray detector 1220 is mounted to a stand-type mount 1230 according to the stand-type scan mode selected by a user. Since the method by which the an X-ray apparatus obtains current positional information regarding the X-ray detector 1220 is described with reference to FIGS. 4 through 8, detailed description thereof will be omitted.

An X-ray apparatus may determine whether X-ray scanning may be performed according to a scan mode selected based on a user input, based on the current position of the X-ray detector 1220. In the embodiment shown in FIG. 12A, the X-ray apparatus may determine whether the X-ray detector 1220 is currently mounted to the stand-type mount 1230 and determine that X-ray scanning may be performed according to the stand-type scan mode selected based on the user input.

The X-ray apparatus may display information regarding the determined X-ray scanning possibility in the form of a user interface 1210A. In the embodiment shown in FIG. 12A, the X-ray apparatus may display a scanning possible icon 1240.

Figure 12B:
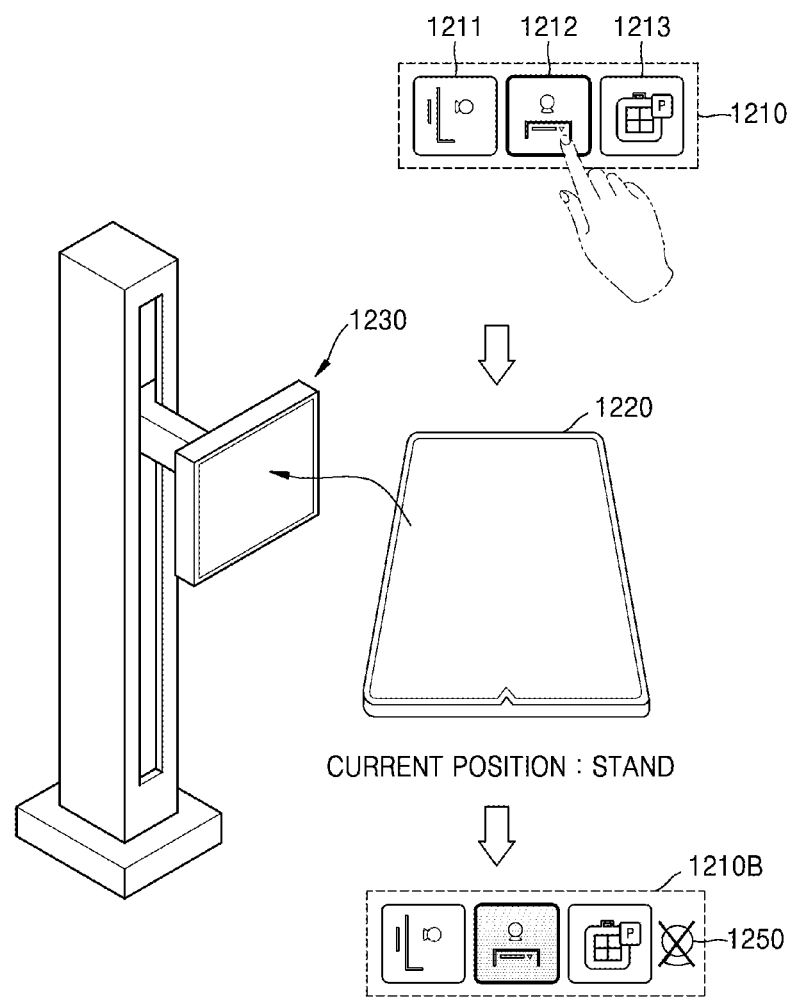

Referring to FIG. 12B, an X-ray apparatus displays the user interface 1210 including the stand-type scan mode icon 1211, the table-type scan mode icon 1212, and the portable-type scan mode icon 1213 according to FIG. 12A and may receive a user input for selecting one of a stand-up type scan mode, a table-type scan mode, and a portable-type scan mode via the displayed user interface 1210. In the embodiment shown in FIG. 12B, the X-ray apparatus may receive a user input for selecting the table-type scan mode icon 1212. The X-ray apparatus may determine whether the X-ray detector 1220 is mounted to a table-type mount according to the table-type scan mode selected based on the user input.

The X-ray apparatus may determine that the currently sensed position of the X-ray detector 1220 is the stand-type mount 1230 instead of the table-type mount. Therefore, the X-ray apparatus may determine whether X-ray scanning may be performed according to the scan mode selected based on a user input, that is, the table-type scan mode, based on the current position and the mounting direction of the X-ray detector 1220. In the embodiment shown in FIG. 12B, the X-ray apparatus may determine that the X-ray detector 1220 is currently mounted to the stand-type mount 1230 and determine that X-ray scanning may not be performed according to the table-type scan mode selected based on the user input.

The X-ray apparatus may display a user interface 1210B that includes a scanning impossible icon 1250.

Figure 12C:
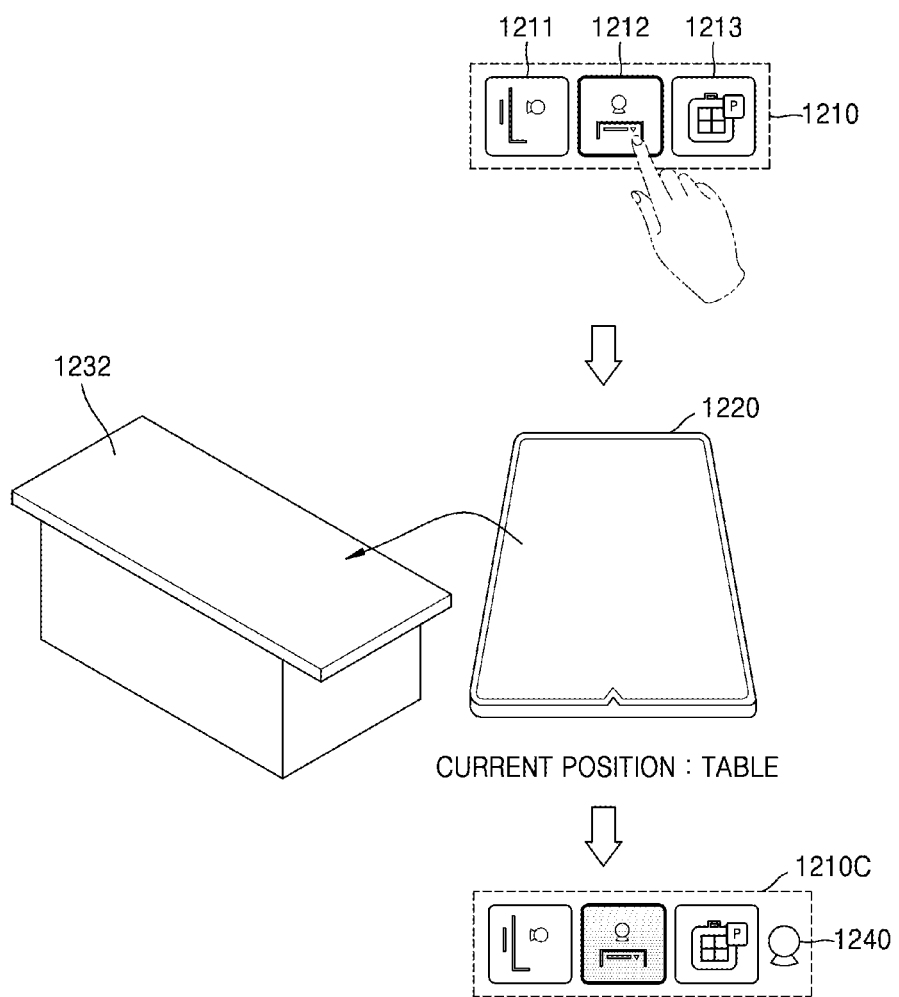

Referring to FIG. 12C, the X-ray apparatus may receive a user input for selecting the table-type scan mode icon 1212 via the user interface 1210 and, according to the table-type scan mode selected based on the received user input, may determine the current position of the X-ray detector 1220. According to an embodiment of the present disclosure, the X-ray apparatus may determine whether the X-ray detector 1220 is mounted to a table-type mount 1232.

In the embodiment shown in FIG. 12C, the X-ray apparatus determines that the currently sensed position of the X-ray detector 1220 is the table-type mount 1232 and X-ray scanning may be performed according to the table-type scan mode selected based on the user input. In this example, the X-ray apparatus may display the scanning possible icon 1240 on a user interface 1210C.

Figure 12D:
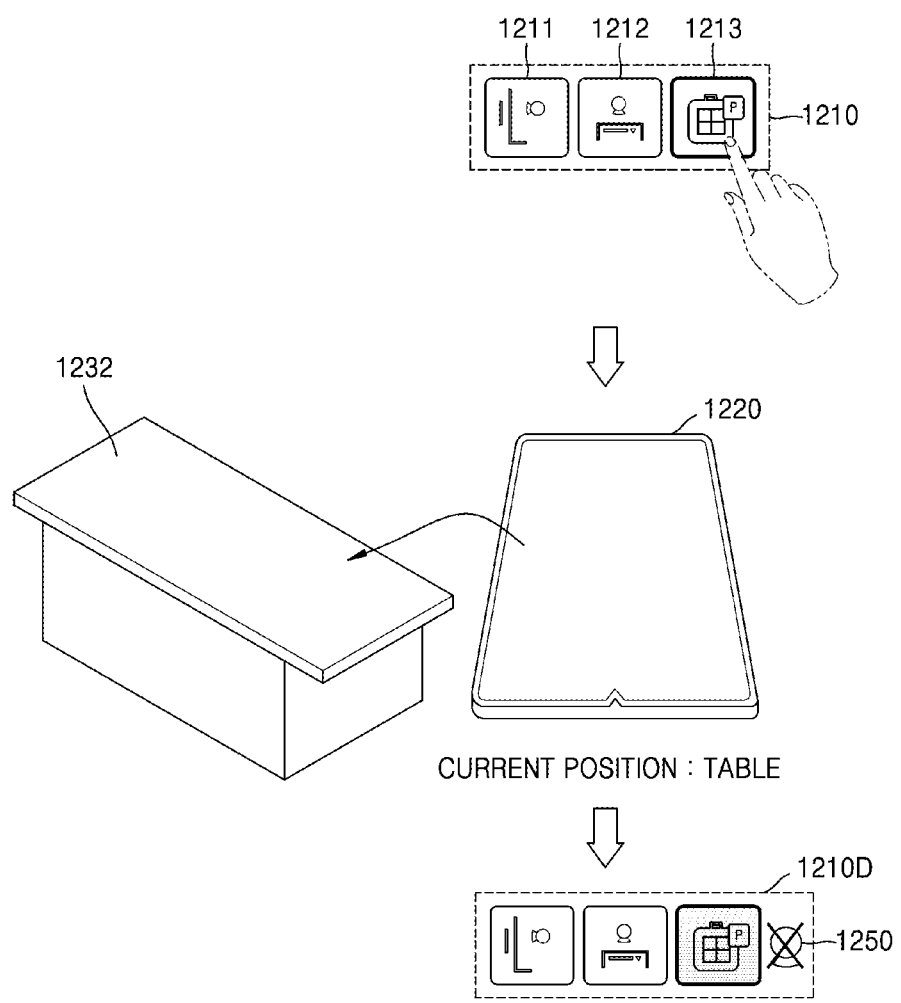

Referring to FIG. 12D, the X-ray apparatus may receive a user input for selecting the portable-type scan mode icon 1213 via the user interface 1210 and, according to the portable-type scan mode selected based on the received user input, may determine the current position of the X-ray detector 1220. According to an embodiment of the present disclosure, the X-ray apparatus may determine whether the X-ray detector 1220 is mounted to neither the stand-type mount 1230 (refer to FIGS. 12A and 12B) nor the table-type mount 1232.

In the embodiment shown in FIG. 12D, the X-ray detector 1220 may be mounted to the table-type mount 1232. Therefore, the X-ray apparatus may determine that the X-ray scanning may not be performed according to the portable scan mode selected based on the user input and display the scanning impossible icon 1250 on a user interface 1210D.

In the embodiment shown in FIGS. 12A through 12D, the X-ray apparatus displays whether the X-ray scanning may be performed according to a scan mode selected based on a user input by using the scanning possible icon 1240 or the scanning impossible icon 1250, thereby reducing effort of a user to determine a current position and a mounting direction of the X-ray detector 1220 and improving user convenience.

Figure 13:
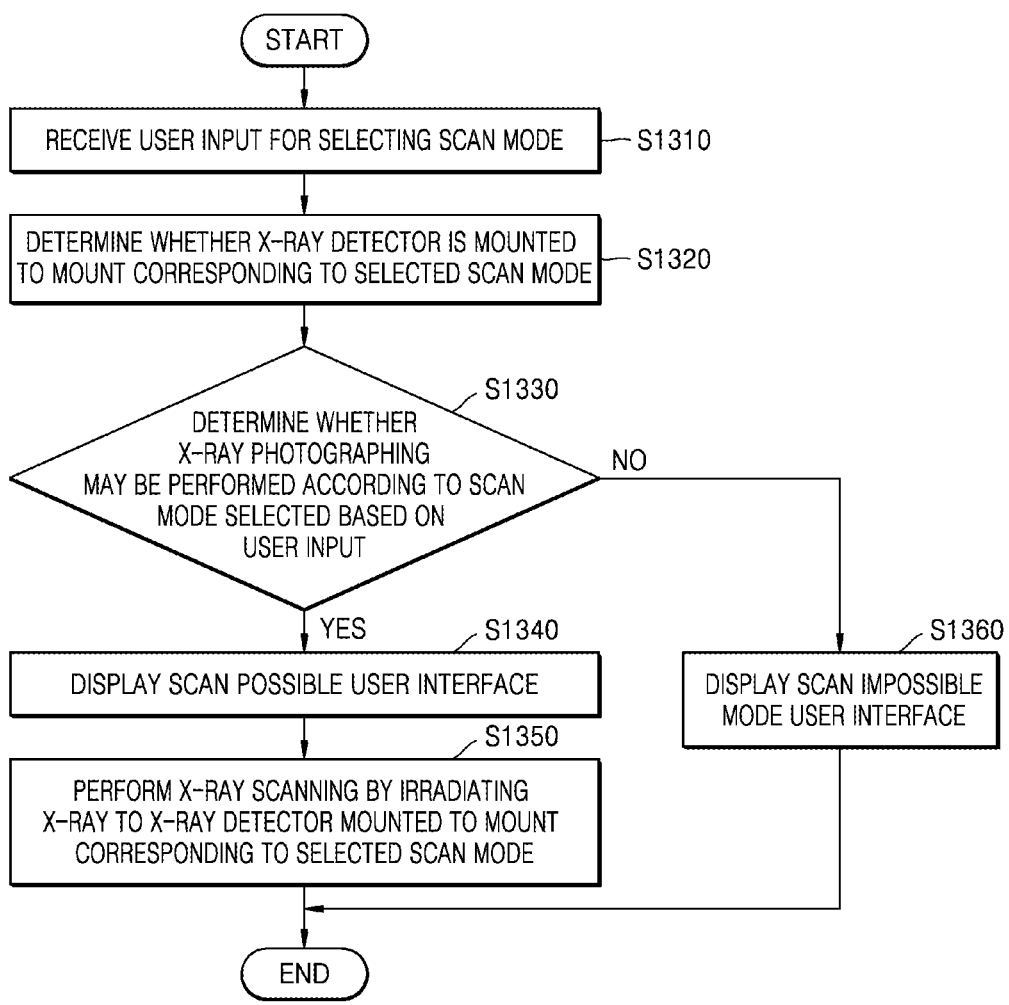
FIG. 13 illustrates a method by which an X-ray detector according to an embodiment determines whether X-ray scanning may be performed according to a scan mode selected based on a user input.

FIG. 13 illustrates a method by which an X-ray detector according to an embodiment determines whether X-ray scanning may be performed according to a scan mode selected based on a user input.

In operation S1310, the X-ray apparatus receives a user input for selecting a scan mode. According to an embodiment of the present disclosure, a workstation included in the X-ray apparatus may display scan mode icons for receiving a user input for selecting a scan mode. The scan mode icon may include a stand-type scanning icon, a table-type scanning icon, a portable-type scanning icon, and a mounted direction icon.

In operation S1320, the X-ray apparatus determines whether an X-ray detector is mounted to a mount according to a selected scan mode. According to an embodiment of the present disclosure, when the X-ray apparatus receives a user input for selecting the stand-type scanning icon, the X-ray apparatus may determine whether the X-ray detector is mounted to a stand-type mount. Since the method by which the X-ray detector obtains positional information regarding a plurality of X-ray detectors is described above with reference to FIGS. 4 through 8, detailed description thereof will be omitted.

According to an embodiment of the present disclosure, the X-ray apparatus determines a direction in which an X-ray detector is mounted to a mount and displays information regarding the determined mounted direction with an icon including at least one of letters, numbers, symbols, and images.

In operation S1330, the X-ray apparatus determines whether X-ray scanning may be performed according to a scan mode selected based on a user input. For example, when the X-ray apparatus receives a user input for selecting the stand-type scan mode, the X-ray apparatus determines whether an X-ray detector is mounted to a stand-type mount according to the selected stand-type scan mode and determines whether X-ray scanning may be performed according to the selected stand-type scan mode.

When it is determined in operation S1340 that X-ray scanning may be performed according to the scan mode selected based on the user input (YES), the X-ray apparatus displays a scanning possible user interface. According to an embodiment of the present disclosure, the workstation included in the X-ray apparatus may display a scanning possible icon indicating that X-ray photography may be performed according to the scan mode selected by the user input.

In operation S1350, the X-ray apparatus irradiates an X-ray to the X-ray detector mounted to the mount corresponding to the selected scan mode, thereby performing X-ray scanning.

When it is determined in operation S1360 that the X-ray scanning may not be performed according to the scan mode selected based on the user input (NO), the X-ray apparatus displays a scanning impossible user interface. According to an embodiment of the present disclosure, the workstation included in the X-ray apparatus may display a scanning impossible icon indicating that the X-ray scanning may not be performed according to the scan mode selected based on the user input.

Figure 14:
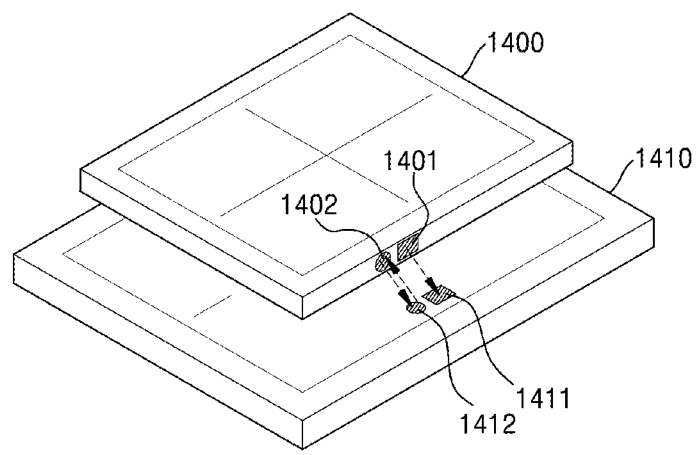
FIG. 14 illustrates a diagram for describing a method of mounting an X-ray detector to a mount, according to an embodiment of the present disclosure.

FIG. 14 illustrates a method of mounting an X-ray detector 1400 to a mount 1410, according to an embodiment of the present disclosure.

Referring to FIG. 14, the X-ray detector 1400 may include a light emitting element 1401 and a reflective member 1402, and a mount 1410 may include a light color sensor 1411 and a light intensity sensor 1412.

The light emitting element 1401 may emit light of a certain color assigned to the X-ray detector 1400. The light emitting element 1401 may include at least one of, for example, a light emitting diode, a semiconductor laser, and a solid state laser. According to an embodiment of the present disclosure, the light emitting element 1401 may emit light of a color assigned by the workstation.

The reflective member 1402 may include a material having a material property of reflecting light. The reflective member 1402 may reflect light emitted by the light intensity sensor 1412 back toward the light intensity sensor 1412 through total reflection. The reflective member 1402 may include at least one of, for example, transparent plastic, ceramic, and transparent glass, but is not limited thereto. According to an embodiment of the present disclosure, the reflective member 1402 may include a metal having a reflective material property of reflecting light, that is, at least one of gold (Au), silver (Ag), copper (Cu), and aluminum (Al). However, the present disclosure is not limited thereto. According to an embodiment of the present disclosure, the reflective member 1402 may include a reflective sticker that changes wavelength of reflected light.

The light color sensor 1411 may be disposed in the mount 1410. Although FIG. 14 shows the one light color sensor 1411, it is merely for convenience of explanation, and a plurality of light color sensors 1411 may be disposed in the mount 1410. The light color sensor 1411 may sense wavelength of light emitted by the light emitting element 1401 and detect color of the light according to the sensed wavelength of the light.

The light intensity sensor 1412 may be disposed adjacent to the light color sensor 1411 in the mount 1410. The light intensity sensor 1412 may include a light emitting element that emits light. Light emitted by the light intensity sensor 1412 may be reflected by the reflective member 1402 included in the X-ray detector 1400 and then reflected back toward the light intensity sensor 1412. The light intensity sensor 1412 may sense intensity of the light reflected by the reflective member 1402.

In the embodiment shown in FIG. 14, the mount 1410 to which the X-ray detector 1400 is mounted may sense color of light emitted by the light emitting element 1401 of the X-ray detector 1400 via the light color sensor 1411 and may sense intensity of light reflected by the reflective member 1402 of the X-ray detector 1400 via the light intensity sensor 1412. The mount 1410 may recognize identification information regarding the X-ray detector 1400 that emits light of a particular color by sensing wavelength of light emitted by the X-ray detector 1400 and recognize a direction in which the X-ray detector 1400 is mounted to the mount 1410 based on intensity of light reflected by the X-ray detector 1400.

Meanwhile, the disclosed embodiments may be embodied in the form of a computer-readable recording medium storing instructions and data executable by a computer. The command may be stored in the form of program code, and, when executed by the processor, may generate a certain program module to perform a certain operation. Furthermore, when executed by a processor, the instructions may perform certain operations of the disclosed embodiments.

It should be understood that embodiments described herein should be considered in a descriptive sense only and not for purposes of limitation. Descriptions of features or aspects within each embodiment should typically be considered as available for other similar features or aspects in other embodiments.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An X-ray apparatus comprising:
    at least one X-ray detector configured to receive X-rays transmitted through an object, wherein the at least one X-ray detector respectively comprises a light emitting element configured to emit light of colors according to identification information of each of the at least one X-ray detector;
    a plurality of mounts to which the at least one X-ray detector is mountable;
    a light color sensor disposed on each of the plurality of mounts and configured to detect a color of a light emitted by the light emitting element; and
    a controller configured to receive color information from the light color sensor, acquire a first identification information of a first X-ray detector based on the received color information, acquire positional information of a first mount, and determine a position of the first X-ray detector based on the positional information of the first mount.

2. The X-ray apparatus of claim 1, wherein the light emitting element includes at least one light emitting diode (LED).

3. The X-ray apparatus of claim 1, wherein the plurality of mounts comprise a stand-type mount or a table-type mount, and
    wherein the controller is configured to acquire the positional information of the first mount from among the stand-type and mount table-type mount.

4. The X-ray apparatus of claim 3, wherein the controller is further configured to detect a positional information of a second X-ray detector mounted to neither the stand-type mount nor the table-type mount.

5. The X-ray apparatus of claim 1, further comprising:
    a display configured to display a user interface (UI) representing the identification information of the first X-ray detector and position of the first X-ray detector by at least one of letters, numbers, symbols, colors, and images.

6. A method for operating an X-ray apparatus, the method comprising:
    receiving, using at least one X-ray detector, X-rays transmitted through an object, wherein the at least one X-ray detector respectively comprises a light emitting element configured to emit light of colors according to identification information of each of the at least one X-ray detector;
    receiving, from a light sensor disposed on a plurality of mounts to which the at least one X-ray detector is mountable, color information of a light emitted by the light emitting element disposed on a first X-ray detector;
    acquiring, by a controller, a first identification information of the first X-ray detector based on the received color information;
    acquiring, by the controller, a first positional information of a first mount from among the plurality of mounts when the first X-ray detector is coupled to the first mount; and
    determining, by the controller, a position of the first X-ray detector based on the positional information of the first mount.

7. The method of claim 6, wherein the plurality of mounts comprise a stand-type mount or a table-type mount, and
    wherein the acquiring the positional information of the first mount comprises acquiring the positional information of the first mount from among the stand-type and mount table-type mount.

8. The method of claim 7, further comprising:
    detecting, by the controller, a positional information of a second X-ray detector mounted to neither the stand-type mount nor the table-type mount.

9. The method of claim 6, further comprising:
    receiving the identification information regarding each of the at least one X-ray detector from the at least one X-ray detector,
    wherein the identification information comprises at least one of information including at least one of MAC addresses and serial numbers of the at least one X-ray detector and specification information including at least one of sizes of the at least one X-ray detector and types of mounts for mounting the at least one X-ray detector.

10. The method of claim 6, further comprising:
    assigning different colors of light to each of the at least one X-ray detector according to the identification information; and
    transmitting information regarding the assigned colors of light to each of the at least one X-ray detector.

11. The method of claim 6, further comprising:
    displaying, by a display apparatus, a user interface (UI) representing the identification information of the first X-ray detector and position of the first X-ray detector by at least one of letters, numbers, symbols, colors, and images.

12. An X-ray apparatus comprising:
    at least one X-ray detector configured to receive X-rays transmitted through an object, wherein the at least one X-ray detector respectively comprises a light emitting element configured to emit light of assigned color;
    a plurality of mounts to which the at least one X-ray detector is mountable;
    a light color sensor disposed on each of the plurality of mounts and configured to detect a color of a light emitted by the light emitting element; and
    a workstation comprising:
        a controller configured to assign colors of light to each of the at least one X-ray detector according to identification information of the each of the at least one X-ray detector, receive color information from the light color sensor, acquire the identification information of each of the at least one X-ray detector based on the received color information, acquire a positional information of each of the plurality of mounts, and determine a position of a first X-ray detector mounted on a first mount from among the plurality of mounts based on acquired positional information of the first mount.

13. The X-ray apparatus of claim 12,
    wherein each of the at least one X-ray detector further comprises a communicator configured to transmit the identification information regarding each of the at least one X-ray detector to the workstation.

14. The X-ray apparatus of claim 12,
    wherein the identification information comprises at least one of information including at least one of MAC addresses and serial numbers of the at least one X-ray detector and specification information including at least one of sizes of the at least one X-ray detector and types of mounts for mounting the at least one X-ray detector.

15. The X-ray apparatus of claim 12,
    wherein the workstation further comprises:

a communicator configured to receive the identification information from each of the at least one X-ray detector, and wherein the controller is further configured to assign different colors of light to each of the at least one X-ray detector according to the received identification information.

16. The X-ray apparatus of claim 12, further comprising:
a plurality of light intensity sensor attached on each of the plurality of mounts, disposed apart from each other, and configured to sense an intensity of light emitted by the light emitting element;

wherein the controller is further configured to acquire information regarding a direction in which the first X-ray detector is mounted to the first mount based on intensity information received from each of the plurality of light intensity sensor.

17. The X-ray apparatus of claim 16, wherein the controller is further configured to acquire directional information indicating whether the first X-ray detector is mounted to the first mount in a direction of a vertical orientation or a horizontal orientation.

18. An X-ray apparatus comprising:
at least one X-ray detector configured to receive X-rays transmitted through an object, wherein the at least one X-ray detector respectively comprises a light emitting element configured to emit light of colors according to identification information of the each of the at least one X-ray detector;

a plurality of mounts to which the at least one X-ray detector is mountable;

a light color sensor disposed on each of the plurality of mounts and configured to detect a color of a light emitted by the light emitting element; and a workstation comprising:
a user input interface configured to receive a user input for selecting a scan mode for performing X-ray scanning using any one of a stand-type mount, a table-type mount, and a portable type X-ray detector, and a controller configured to select the scan mode based on the user input received by the user input interface, receive a color information from the light color sensor, acquire a first identification information of a first X-ray detector based on the received color information, acquire a position of the first X-ray detector based on a positional information of a first mount from among the plurality of mounts when the first X-ray detector is coupled to the first mount, and determine whether it is possible to perform X-ray photographing according to the scan mode selected based on the user input, based on the acquired position of the first X-ray detector.

19. The X-ray apparatus of claim 18, wherein the workstation further comprises:
a display configured to display a user interface (UI) regarding the information indicating the determined possibility of X-ray photographing.

* * * * *